US007371555B2

(12) United States Patent
Boesten et al.

(10) Patent No.: US 7,371,555 B2
(45) Date of Patent: May 13, 2008

(54) POLYPEPTIDES HAVING α-H-α-AMINO ACID AMIDE RACEMASE ACTIVITY AND NUCLEIC ACIDS ENCODING THE SAME

(75) Inventors: Wilhelmus Hubertus Joseph Boesten, Sittard (NL); Petronella Catharina Raemakers-Franken, Budel (NL); Theodorus Sonke, Guttecoven (NL); Gerrit Jan Willem Euverink, Hoogezand (NL); Pieter Grijpstra, Ee (NL)

(73) Assignee: DSM IP Assets B.V., Te Heerlen (NL)

( * ) Notice: Subject to any disclaimer, the term of this patent is extended or adjusted under 35 U.S.C. 154(b) by 293 days.

(21) Appl. No.: 10/732,011

(22) Filed: Dec. 9, 2003

(65) Prior Publication Data

US 2004/0248274 A1    Dec. 9, 2004

Related U.S. Application Data

(60) Provisional application No. 60/437,223, filed on Dec. 31, 2002.

(30) Foreign Application Priority Data

| Jun. 14, 2002 | (EP) | .................................. 02100711 |
| Dec. 20, 2002 | (EP) | .................................. 02080631 |
| Jun. 13, 2003 | (WO) | ..................... PCT/NL03/00423 |

(51) Int. Cl.
| C12N 9/90 | (2006.01) |
| C12N 15/70 | (2006.01) |
| C12N 5/16 | (2006.01) |
| C12P 21/06 | (2006.01) |
| C12P 13/04 | (2006.01) |
| C07H 21/04 | (2006.01) |

(52) U.S. Cl. ................... 435/233; 435/69.1; 435/320.1; 435/106; 435/325; 536/23.2

(58) Field of Classification Search .................. 435/233
See application file for complete search history.

(56) References Cited

U.S. PATENT DOCUMENTS 5,100,782 A    3/1992   Klages et al.

FOREIGN PATENT DOCUMENTS

| EP | 0 383 403 | 8/1990 |
| EP | 0 494 716 | 7/1992 |
| JP | 63129984 A | 6/1988 |
| WO | WO-86/07386 | 12/1986 |
| WO | WO 00/66751 | 11/2000 |
| WO | WO-2005/080584 | 9/2005 |

OTHER PUBLICATIONS

Ahmed et al., Agric. Biol. Chem. (1983) 47:1887-1893.
Duchatreau et al., J. Chromatogr. (1992) 623:237-245.
Fukumura et al., Agric. Biol. Chem. (1997) 41:1509-1510.
Gentz et al., Proc. Natl. Acad. Sci. USA (1989) 86:821-824.
Makrides, Microbiological Reviews (1996) 60(3):512-538.
Naoko et al., Biochemistry of Vitamin B6 (1987) p. 449-452.
Sonke et al., Stereoselective Biocatalysis (2000) (ed. Patel) Dekker, New York, pp. 23-58.
Ahmed et al., Agricultural and Biological Chemistry (1983) 47(8):1887-1894.
Asano and Yamaguchi, Journal of Molecular Catalysis B: Enzymatic (2005) 36:22-29 (abstract).
Asano and Yamaguchi, J. Am. Chem. Soc. (2005) 127:7696-7697.
Fukumura, Agricultural and Biological Chemistry (1977) 41(8):1321-1326.
International Search Report for PCT/NL03/00423, mailed on Aug. 25, 2003, 3 pages.
Kamphuis et al., Chirality in Industry, Collins et al. (eds.), John Wiley & Sons, Ltd. (1992) pp. 187-208.
Kaptein et al., Tetrahedron (2001) 57(30):6567-6577.
Kato et al., Tetrahedron (1989) 45(18):5743-5754.
Tornøe et al., Tetrahedron: Asymmetry (2000) 11(5):1239-1248.
Van Den Tweel et al., Applied Microbiology and Biotechnology (1993) 39(3):296-300.
Hermes et al. "Metabolism of amino acid amides in *Pseudomonas putida* ATCC 12633" Appl. Microbiol. Biotechnol. 40:519-525 (1993).
Wolf et al. "A biocatalytic route to enantiomerically pure unsaturated α-Hα-amino acids" Adv. Synth. Catal. 343:662-674 (2001).

*Primary Examiner*—Ponnathapu Achutamurthy
*Assistant Examiner*—Iqbal Chowdhury
(74) *Attorney, Agent, or Firm*—Nixon & Vanderhye P.C.

(57) ABSTRACT

The invention relates to isolated polypeptides having α-H-α-amino acid amide racemase activity and nucleic acids encoding the same. The invention also relates to vectors and host cells comprising the nucleic acids according to the invention. The invention also relates to methods of producing and using the polypeptides according to the invention. The invention also relates to a method for isolating polypeptides having α-H-α-amino acid amide racemase activity, for isolating nucleic acids encoding the same and for isolating microorganisms comprising polypeptides having α-H-α-amino acid amide racemase activity. The invention also relates to new microorganisms comprising polypeptides having α-H-α-amino acid amide racemase activity.

6 Claims, No Drawings

SEQUENCE LISTING

<160> NUMBER OF SEQ ID NOS: 9

<210> SEQ ID NO 1
<211> LENGTH: 1501
<212> TYPE: DNA
<213> ORGANISM: Ochrobactrum anthropi IA NCIMB 41129
<220> FEATURE:
<221> NAME/KEY: CDS
<222> LOCATION: (98)..(1417)
<223> OTHER INFORMATION: Amino Acid Amide Racemase encoding sequence

<400> SEQUENCE: 1

```
attcgtcagg atcttgtatc gacgccacag ggcatagccg aatggacaga tcgtctggca      60
aaggctttgc ttggtcagtc acaccagggg tgatgtg atg caa aca ccg ctt tca      115
                                        Met Gln Thr Pro Leu Ser
                                        1               5 ttg cgt gag cgc gac gca cgg gtc att gca gaa ata gga cgc tta cgg      163
Leu Arg Glu Arg Asp Ala Arg Val Ile Ala Glu Ile Gly Arg Leu Arg
        10                  15                  20 ttt tca cct ttg agc ctg atc ggc ggc aag ggc aac agg ctg ata gag      211
Phe Ser Pro Leu Ser Leu Ile Gly Gly Lys Gly Asn Arg Leu Ile Glu
            25                  30                  35 gaa ggt ggg cgt tcc atc ctt gat ctg tct ggc tcc gcc gga cct gct      259
Glu Gly Gly Arg Ser Ile Leu Asp Leu Ser Gly Ser Ala Gly Pro Ala
    40                  45                  50 gct ctg ggg tat ggt cat ccg gct att gtt gaa gcg gtt gaa aaa tct      307
Ala Leu Gly Tyr Gly His Pro Ala Ile Val Glu Ala Val Glu Lys Ser
55                  60                  65                  70 gtt cgc gat atg gcg ggt gca agc ttg ttg ctt tac ccg aac gag gct      355
Val Arg Asp Met Ala Gly Ala Ser Leu Leu Leu Tyr Pro Asn Glu Ala
                75                  80                  85 gcc gtt tcg ctt gcc gaa gac ttg ctg cgc atc acc ccc ggc aat ggc      403
Ala Val Ser Leu Ala Glu Asp Leu Leu Arg Ile Thr Pro Gly Asn Gly
            90                  95                  100 gag cgt cgc gtg tgg ttt ggt cat tcg gga tca gat gcc aat gat tgt      451
Glu Arg Arg Val Trp Phe Gly His Ser Gly Ser Asp Ala Asn Asp Cys
        105                 110                 115 gcg gta cgc gta cta act gcc gcc acc aag cgc tca cgt atc ata tct      499
Ala Val Arg Val Leu Thr Ala Ala Thr Lys Arg Ser Arg Ile Ile Ser
    120                 125                 130 ttt atc ggt tct tac cac ggt aat ctg aca ggc tcg atg ggg ata agc      547
Phe Ile Gly Ser Tyr His Gly Asn Leu Thr Gly Ser Met Gly Ile Ser
135                 140                 145                 150 ggt cac act gcg atg aca cat aca ttg ccg cgc ccc ggt gta ttg ctg      595
Gly His Thr Ala Met Thr His Thr Leu Pro Arg Pro Gly Val Leu Leu
                155                 160                 165 ttg cca tat cct gat ccg ttc agg ccg cgc ttt tct gcg gaa gcc gtg      643
Leu Pro Tyr Pro Asp Pro Phe Arg Pro Arg Phe Ser Ala Glu Ala Val
            170                 175                 180 ctt gaa ctt ctc gat tat cac ttc gct aca agc tgc ccg cca gag caa      691
Leu Glu Leu Leu Asp Tyr His Phe Ala Thr Ser Cys Pro Pro Glu Gln
        185                 190                 195 gtt gcg gct gtg ttc atc gag ccg atc tta tca gat ggt ggt ctc gtc      739
Val Ala Ala Val Phe Ile Glu Pro Ile Leu Ser Asp Gly Gly Leu Val
    200                 205                 210 gtg cct ccg ccg gcc ttt tta gaa gca ttg cag gat cgt tgt cgc aag      787
Val Pro Pro Pro Ala Phe Leu Glu Ala Leu Gln Asp Arg Cys Arg Lys
215                 220                 225                 230 cat gga att ctg gtg gta gtc gat gag gtc aag gtt ggc ctt ggc cga      835
```

```
                His Gly Ile Leu Val Val Asp Glu Val Lys Val Gly Leu Gly Arg
                            235                 240                 245 acc ggg ctg atg cat tgt ttc cag cat gaa ggg ctt gag cct gac atg         883
Thr Gly Leu Met His Cys Phe Gln His Glu Gly Leu Glu Pro Asp Met
            250                 255                 260 gtg gtg ttc gga aaa ggt ctt gga ggt ggt tta cct ctt tct gcg gtt         931
Val Val Phe Gly Lys Gly Leu Gly Gly Gly Leu Pro Leu Ser Ala Val
            265                 270                 275 gtt gga ccg caa tgg gtg atg gat cac gcg cct gcg ttt gtg ttg caa         979
Val Gly Pro Gln Trp Val Met Asp His Ala Pro Ala Phe Val Leu Gln
            280                 285                 290 acc aca gcc gga aat cca gtg gcg act gct gcc ggt cgc gct gta ctc        1027
Thr Thr Ala Gly Asn Pro Val Ala Thr Ala Ala Gly Arg Ala Val Leu
295                 300                 305                 310 aat acg att gag agg caa gga ctt gcc caa cga tcg gag cgg gtt ggg        1075
Asn Thr Ile Glu Arg Gln Gly Leu Ala Gln Arg Ser Glu Arg Val Gly
                315                 320                 325 ggg att ttc gca gat cgc ctg cgc cgg ctc agc gat aag cat tcc atc        1123
Gly Ile Phe Ala Asp Arg Leu Arg Arg Leu Ser Asp Lys His Ser Ile
            330                 335                 340 ata ggg gat gta cgc ggc aga ggg cta gcg att ggc gtt gat ctc gta        1171
Ile Gly Asp Val Arg Gly Arg Gly Leu Ala Ile Gly Val Asp Leu Val
            345                 350                 355 agt gat cgt gga tca cgt gag ccg gct ccg gta acg acg acc gcg aaa        1219
Ser Asp Arg Gly Ser Arg Glu Pro Ala Pro Val Thr Thr Thr Ala Lys
            360                 365                 370 att ata tat cgc ggc tat caa ctc ggc gca gct ttt acc tat gtc ggc        1267
Ile Ile Tyr Arg Gly Tyr Gln Leu Gly Ala Ala Phe Thr Tyr Val Gly
375                 380                 385                 390 ctc aat gcc aat gtt ctg gaa ttc atg ccc ccg ttg act ttg acc gag        1315
Leu Asn Ala Asn Val Leu Glu Phe Met Pro Pro Leu Thr Leu Thr Glu
                395                 400                 405 ccg gaa ata gac gaa gca gcg gac atc gtt gat cag gcc att ggc gat        1363
Pro Glu Ile Asp Glu Ala Ala Asp Ile Val Asp Gln Ala Ile Gly Asp
            410                 415                 420 gtt ctg gat ggg aag gtg gct gat agc gat gtc gcc cat ttt atg atg        1411
Val Leu Asp Gly Lys Val Ala Asp Ser Asp Val Ala His Phe Met Met
            425                 430                 435 tgg taa ggatctgggg ctgttgatac tcaagcggcg aagagctcag cgaacattat        1467
Trp ggcgaactgt ttctggctga aaaccctcct ctta                                  1501

<210> SEQ ID NO 2
<211> LENGTH: 439
<212> TYPE: PRT
<213> ORGANISM: Ochrobactrum anthropi IA NCIMB 41129

<400> SEQUENCE: 2

Met Gln Thr Pro Leu Ser Leu Arg Glu Arg Asp Ala Arg Val Ile Ala
1               5                   10                  15

Glu Ile Gly Arg Leu Arg Phe Ser Pro Leu Ser Leu Ile Gly Gly Lys
            20                  25                  30

Gly Asn Arg Leu Ile Glu Glu Gly Gly Arg Ser Ile Leu Asp Leu Ser
        35                  40                  45

Gly Ser Ala Gly Pro Ala Ala Leu Gly Tyr Gly His Pro Ala Ile Val
    50                  55                  60

Glu Ala Val Glu Lys Ser Val Arg Asp Met Ala Gly Ala Ser Leu Leu
65                  70                  75                  80
```

```
Leu Tyr Pro Asn Glu Ala Ala Val Ser Leu Ala Glu Asp Leu Leu Arg
                 85                  90                  95

Ile Thr Pro Gly Asn Gly Glu Arg Arg Val Trp Phe Gly His Ser Gly
            100                 105                 110

Ser Asp Ala Asn Asp Cys Ala Val Arg Val Leu Thr Ala Ala Thr Lys
        115                 120                 125

Arg Ser Arg Ile Ile Ser Phe Ile Gly Ser Tyr His Gly Asn Leu Thr
130                 135                 140

Gly Ser Met Gly Ile Ser Gly His Thr Ala Met Thr His Thr Leu Pro
145                 150                 155                 160

Arg Pro Gly Val Leu Leu Pro Tyr Pro Asp Pro Phe Arg Pro Arg
                165                 170                 175

Phe Ser Ala Glu Ala Val Leu Glu Leu Leu Asp Tyr His Phe Ala Thr
                180                 185                 190

Ser Cys Pro Pro Glu Gln Val Ala Ala Val Phe Ile Glu Pro Ile Leu
            195                 200                 205

Ser Asp Gly Gly Leu Val Val Pro Pro Ala Phe Leu Glu Ala Leu
        210                 215                 220

Gln Asp Arg Cys Arg Lys His Gly Ile Leu Val Val Asp Glu Val
225                 230                 235                 240

Lys Val Gly Leu Gly Arg Thr Gly Leu Met His Cys Phe Gln His Glu
                245                 250                 255

Gly Leu Glu Pro Asp Met Val Val Phe Gly Lys Gly Leu Gly Gly Gly
                260                 265                 270

Leu Pro Leu Ser Ala Val Val Gly Pro Gln Trp Val Met Asp His Ala
            275                 280                 285

Pro Ala Phe Val Leu Gln Thr Thr Ala Gly Asn Pro Val Ala Thr Ala
        290                 295                 300

Ala Gly Arg Ala Val Leu Asn Thr Ile Glu Arg Gln Gly Leu Ala Gln
305                 310                 315                 320

Arg Ser Glu Arg Val Gly Gly Ile Phe Ala Asp Arg Leu Arg Arg Leu
                325                 330                 335

Ser Asp Lys His Ser Ile Ile Gly Asp Val Arg Gly Arg Gly Leu Ala
            340                 345                 350

Ile Gly Val Asp Leu Val Ser Asp Arg Gly Ser Arg Glu Pro Ala Pro
        355                 360                 365

Val Thr Thr Thr Ala Lys Ile Ile Tyr Arg Gly Tyr Gln Leu Gly Ala
    370                 375                 380

Ala Phe Thr Tyr Val Gly Leu Asn Ala Asn Val Leu Glu Phe Met Pro
385                 390                 395                 400

Pro Leu Thr Leu Thr Glu Pro Glu Ile Asp Glu Ala Ala Asp Ile Val
                405                 410                 415

Asp Gln Ala Ile Gly Asp Val Leu Asp Gly Lys Val Ala Asp Ser Asp
            420                 425                 430

Val Ala His Phe Met Met Trp
        435

<210> SEQ ID NO 3
<211> LENGTH: 436
<212> TYPE: DNA
<213> ORGANISM: Arthrobacter nicotianae NCIMB 41126

<400> SEQUENCE: 3
cggcgtgctt aacacatgca agtcgaacga tgatccccag cttgctgggg ggattagtgg    60
```

```
cgaacgggtg agtaacacgt gagtaacctg cccccgactc tgggataagc ccgggaaact    120
gggtctaata ccggatattc acttccttcc gcatggaggt tggtggaaag gtcttttccg    180
gtcggggatg gactcgcggc ctatcagctt gttggtgggg tagtggccca ccaaggcgac    240
gacgggtagc cggcctgaga gggtgaccgg ccacactggg actgagacac ggcccagact    300
cctacgggag gcagcagtgg ggaatattgc acaatgggcg caagcctgat gcagcgacgc    360
cgcgtgaggg atgacggcct tcgggttgta acctctttc agtagggaag aagcgaaagt    420
gacggtacct gcagaa                                                     436

<210> SEQ ID NO 4
<211> LENGTH: 400
<212> TYPE: DNA
<213> ORGANISM: Agrobacterium rhizogenes Bi NCIMB 41128

<400> SEQUENCE: 4
ggcggcaggc ttaacacatg caagtcgagc gccccgcaag gggagcggca gacgggtgag     60
taacgcgtgg gaatctaccc ttttctacgg aataacgcag ggaaacttgt gctaataccg    120
tatacgccct tcgggggaaa gatttatcgg gaaaggatga gccgcgttg gattagctag    180 ttggtggggt aaaggcctac caaggcgacg atccatagct ggtctgagag gatgatcagc    240
cacattggga ctgagacacg gcccaaactc ctacggagg cagcagtggg gaatattgga    300
caatgggcgc aagcctgatc agccatgcc gcgtgagtga tgaaggccct agggttgtaa    360
agctctttca ccggtgaaga taatgacggt aaccggagaa                          400

<210> SEQ ID NO 5
<211> LENGTH: 381
<212> TYPE: DNA
<213> ORGANISM: Agrobacterium rhizogenes Na NCIMB 41127

<400> SEQUENCE: 5
caggcttaac acatgcaagt cgagcgcccc gcaaggggag cggcagacgg gtgagtaacg     60
cgtgggaatc tacccttttc tacggaataa cgcatggaaa cgtgtgctaa taccgtatga    120 gccctttcggg ggaaagattt atcgggaaag gatgagcccg cgttggatta gctagttggt    180
ggggtaaagg cctaccaagg cgacgatcca tagctggtct gagaggatga tcagccacat    240
tgggactgag acacggccca aactcctacg ggaggcagca gtggggaata ttggacaatg    300 gcgcaagcc tgatccagcc atgccgcgtg agtgatgaag ccctagggt tgtaaagctc    360 tttcaccggt gaagataatg a                                              381

<210> SEQ ID NO 6
<211> LENGTH: 32
<212> TYPE: DNA
<213> ORGANISM: Artificial Sequence
<220> FEATURE:
<223> OTHER INFORMATION: Synthetic DNA

<400> SEQUENCE: 6
gcctcacata tgcaaacacc gctttcattg cg                                   32

<210> SEQ ID NO 7
<211> LENGTH: 39
<212> TYPE: DNA
<213> ORGANISM: Artificial Sequence
<220> FEATURE:
<223> OTHER INFORMATION: Synthetic DNA

<400> SEQUENCE: 7
```

```
gcctcacccg ggttaccaca tcataaaatg ggcgacatc                             39

<210> SEQ ID NO 8
<211> LENGTH: 1454
<212> TYPE: DNA
<213> ORGANISM: Arthrobacter nicotianae NCIMB 41126
<220> FEATURE:
<221> NAME/KEY: CDS
<222> LOCATION: (80)..(1417)
<223> OTHER INFORMATION: Amino Acid Amide Racemase encoding sequence

<400> SEQUENCE: 8
actaaccaaa gaggacattt cgtcatgacc gtcggcggcc gtgagtacgc cgcgttgcgg      60
ggagcgccga ggagggcac atg ctt gaa gac tct ctc tac gcc cgc gac ggg      112
                    Met Leu Glu Asp Ser Leu Tyr Ala Arg Asp Gly
                     1               5                  10 cgc gtt atc gca ggc gta gag aag ctg cgc ttc ttt ccg ctg gag act      160
Arg Val Ile Ala Gly Val Glu Lys Leu Arg Phe Phe Pro Leu Glu Thr
         15                  20                  25 gcc tcc ggc cgg ggc agc atg ctc gtc gag cca ggt ggc agg gaa ttg      208
Ala Ser Gly Arg Gly Ser Met Leu Val Glu Pro Gly Gly Arg Glu Leu
     30                  35                  40 ttc gac ttc agc gcc agc tgg acg gct gca ggg ctg ggg cac ggg aac      256
Phe Asp Phe Ser Ala Ser Trp Thr Ala Ala Gly Leu Gly His Gly Asn
 45                  50                  55 cct gaa atc acc gcg gcc att gca cga gcc gct gtt gat tct ccc ggc      304
Pro Glu Ile Thr Ala Ala Ile Ala Arg Ala Ala Val Asp Ser Pro Gly
 60                  65                  70                  75 gca tct atc ctg tcg gca aca cac tcg gaa gct gtc gga ctg gcc gaa      352
Ala Ser Ile Leu Ser Ala Thr His Ser Glu Ala Val Gly Leu Ala Glu
                 80                  85                  90 cga ctc ctg gac atg gtt ccg acg cga agg tcc ggc ccc ggt ggg cgg      400
Arg Leu Leu Asp Met Val Pro Thr Arg Arg Ser Gly Pro Gly Gly Arg
             95                 100                 105 cgt gtc tat ctt ggc cac gcc gga acc gac tcg aat gat gta gct atc      448
Arg Val Tyr Leu Gly His Ala Gly Thr Asp Ser Asn Asp Val Ala Ile
         110                 115                 120 aga ggc tgc cgc cat gct tcc gga agg cca gga gtc atc gcc ttc gaa      496
Arg Gly Cys Arg His Ala Ser Gly Arg Pro Gly Val Ile Ala Phe Glu
 125                 130                 135 ggc ggg tat cat ggc ggg ctc ggc atc gcc cag cgc ata tcg ggt gtc      544
Gly Gly Tyr His Gly Gly Leu Gly Ile Ala Gln Arg Ile Ser Gly Val
140                 145                 150                 155 cat gtg gat tcc ggc gtt cct gcc gac ccc cat gta gcg ttc gtc ccc      592
His Val Asp Ser Gly Val Pro Ala Asp Pro His Val Ala Phe Val Pro
                 160                 165                 170 tat cct gat ctg ttc cgc ccg cac acg ggt gac ccg gag aca gtt ctg      640
Tyr Pro Asp Leu Phe Arg Pro His Thr Gly Asp Pro Glu Thr Val Leu
             175                 180                 185 ccg gac gtg ctg acg cgc gtc cgg cag aac ctc caa cgg ggc atg acc      688
Pro Asp Val Leu Thr Arg Val Arg Gln Asn Leu Gln Arg Gly Met Thr
         190                 195                 200 gca gcc gtc atc gtc gaa cct ctc ctc tcc gac ggc ggc gtc atc gtg      736
Ala Ala Val Ile Val Glu Pro Leu Leu Ser Asp Gly Gly Val Ile Val
     205                 210                 215 ccg ccc ccg gag ttc ctc cgt ggt cta agg gaa ctg tgc gac gcg cac      784
Pro Pro Pro Glu Phe Leu Arg Gly Leu Arg Glu Leu Cys Asp Ala His
220                 225                 230                 235 aac gca tac ctc atc gtg gac gag gtc aaa gta ggg ctc ggg cgc act      832
Asn Ala Tyr Leu Ile Val Asp Glu Val Lys Val Gly Leu Gly Arg Thr
```

```
                240                 245                 250
ggc agc ctt cac gcc ttc gaa cat gac ggc atc ctg ccg gac att gtc      880
Gly Ser Leu His Ala Phe Glu His Asp Gly Ile Leu Pro Asp Ile Val
            255                 260                 265 acg ctc gga aaa gtc ctt ggt ggc ggg ctc ccc ctt tcc gcg gcc atc      928
Thr Leu Gly Lys Val Leu Gly Gly Gly Leu Pro Leu Ser Ala Ala Ile
            270                 275                 280 ggt ccg tcg gaa gtt ctc gac cgg ccg gtt gcc tcg gcg tta atg acg      976
Gly Pro Ser Glu Val Leu Asp Arg Pro Val Ala Ser Ala Leu Met Thr
285                 290                 295 act aca ggc aat ccc atc tcc tgc gcg gct ggc cgt gcc gca gtc gaa     1024
Thr Thr Gly Asn Pro Ile Ser Cys Ala Ala Gly Arg Ala Ala Val Glu
300                 305                 310                 315 ata gtg tgc aga ggc gac gtc atc cgg aat gcg gcc gag cgc ggc gag     1072
Ile Val Cys Arg Gly Asp Val Ile Arg Asn Ala Ala Glu Arg Gly Glu
                320                 325                 330 caa atc aga gac ctg ctc gcc gcc tat gca aga gaa acc ggg cgg cct     1120
Gln Ile Arg Asp Leu Leu Ala Ala Tyr Ala Arg Glu Thr Gly Arg Pro
            335                 340                 345 ggc gca gcc cac gtt ggt gat gtc cgc ggc cgc ggc ctc tcc atc ggc     1168
Gly Ala Ala His Val Gly Asp Val Arg Gly Arg Gly Leu Ser Ile Gly
            350                 355                 360 atc gag att gtc acg gac cgg gac gaa aat gtc agc gat ccg ggg ctc     1216
Ile Glu Ile Val Thr Asp Arg Asp Glu Asn Val Ser Asp Pro Gly Leu
365                 370                 375 acc gcc aaa gcc gtc tac cgt gcc tgg gag ctt ggc gtg gtc gtg cat     1264
Thr Ala Lys Ala Val Tyr Arg Ala Trp Glu Leu Gly Val Val Val His
380                 385                 390                 395 cca gtg cgc ggc aat gtc ctt gaa ctc aca ccg ccg ctc aca gtg tca     1312
Pro Val Arg Gly Asn Val Leu Glu Leu Thr Pro Pro Leu Thr Val Ser
                400                 405                 410 gca gac gag gtg cag cag gcc atg gac ctc ctg acc tgc gcg cta gat     1360
Ala Asp Glu Val Gln Gln Ala Met Asp Leu Leu Thr Cys Ala Leu Asp
            415                 420                 425 gac gcc gct cgg ggc ctc gtg agc gat gag cag atc gct ccc tat gct     1408
Asp Ala Ala Arg Gly Leu Val Ser Asp Glu Gln Ile Ala Pro Tyr Ala
            430                 435                 440 ggt tgg tga cgtgaaaaaa ccgccggaga gcggaaccgg cgtgagc                1454
Gly Trp
    445

<210> SEQ ID NO 9
<211> LENGTH: 445
<212> TYPE: PRT
<213> ORGANISM: Arthrobacter nicotianae NCIMB 41126

<400> SEQUENCE: 9

Met Leu Glu Asp Ser Leu Tyr Ala Arg Asp Gly Arg Val Ile Ala Gly
1               5                   10                  15

Val Glu Lys Leu Arg Phe Pro Leu Glu Thr Ala Ser Gly Arg Gly
            20                  25                  30

Ser Met Leu Val Glu Pro Gly Gly Arg Glu Leu Phe Asp Phe Ser Ala
        35                  40                  45

Ser Trp Thr Ala Ala Gly Leu Gly His Gly Asn Pro Glu Ile Thr Ala
    50                  55                  60

Ala Ile Ala Arg Ala Ala Val Asp Ser Pro Gly Ala Ser Ile Leu Ser
65                  70                  75                  80

Ala Thr His Ser Glu Ala Val Gly Leu Ala Glu Arg Leu Leu Asp Met
                85                  90                  95
```

-continued

```
Val Pro Thr Arg Arg Ser Gly Pro Gly Gly Arg Val Tyr Leu Gly
                100             105             110

His Ala Gly Thr Asp Ser Asn Asp Val Ala Ile Arg Gly Cys Arg His
            115                 120             125

Ala Ser Gly Arg Pro Gly Val Ile Ala Phe Glu Gly Gly Tyr His Gly
        130             135             140

Gly Leu Gly Ile Ala Gln Arg Ile Ser Gly Val His Val Asp Ser Gly
145             150             155             160

Val Pro Ala Asp Pro His Val Ala Phe Val Pro Tyr Pro Asp Leu Phe
                165             170             175

Arg Pro His Thr Gly Asp Pro Glu Thr Val Leu Pro Asp Val Leu Thr
            180             185             190

Arg Val Arg Gln Asn Leu Gln Arg Gly Met Thr Ala Ala Val Ile Val
        195             200             205

Glu Pro Leu Leu Ser Asp Gly Gly Val Ile Val Pro Pro Glu Phe
    210             215             220

Leu Arg Gly Leu Arg Glu Leu Cys Asp Ala His Asn Ala Tyr Leu Ile
225             230             235             240

Val Asp Glu Val Lys Val Gly Leu Gly Arg Thr Gly Ser Leu His Ala
                245             250             255

Phe Glu His Asp Gly Ile Leu Pro Asp Ile Val Thr Leu Gly Lys Val
            260             265             270

Leu Gly Gly Gly Leu Pro Leu Ser Ala Ala Ile Gly Pro Ser Glu Val
        275             280             285

Leu Asp Arg Pro Val Ala Ser Ala Leu Met Thr Thr Thr Gly Asn Pro
290             295             300

Ile Ser Cys Ala Ala Gly Arg Ala Ala Val Glu Ile Val Cys Arg Gly
305             310             315             320

Asp Val Ile Arg Asn Ala Ala Glu Arg Gly Glu Gln Ile Arg Asp Leu
                325             330             335

Leu Ala Ala Tyr Ala Arg Glu Thr Gly Arg Pro Gly Ala Ala His Val
            340             345             350

Gly Asp Val Arg Gly Arg Gly Leu Ser Ile Gly Ile Glu Ile Val Thr
        355             360             365

Asp Arg Asp Glu Asn Val Ser Asp Pro Gly Leu Thr Ala Lys Ala Val
370             375             380

Tyr Arg Ala Trp Glu Leu Gly Val Val Val His Pro Val Arg Gly Asn
385             390             395             400

Val Leu Glu Leu Thr Pro Pro Leu Thr Val Ser Ala Asp Glu Val Gln
                405             410             415

Gln Ala Met Asp Leu Leu Thr Cys Ala Leu Asp Asp Ala Ala Arg Gly
            420             425             430

Leu Val Ser Asp Glu Gln Ile Ala Pro Tyr Ala Gly Trp
435             440             445
```

POLYPEPTIDES HAVING α-H-α-AMINO ACID AMIDE RACEMASE ACTIVITY AND NUCLEIC ACIDS ENCODING THE SAME

CROSS-REFERENCE TO RELATED APPLICATIONS

This application claims priority to U.S. Provisional Application No. 60/437,223 filed Dec. 31, 2002. This application further claims priority to International Application No. PCT/NL03/00423, filed Jun. 13, 2003; which claims priority to European Application No. 02100711.7, filed Jun. 14, 2002; and European Application No. 02080631.1 filed Dec. 20, 2002. The disclosures of these applications are incorporated herein by reference in their entirety.

TECHNICAL FIELD

The invention relates to isolated polypeptides having α-H-α-amino acid amide racemase activity and nucleic acids encoding the same. The invention also relates to vectors and host cells comprising the nucleic acids according to the invention. The invention also relates to methods of producing and using the polypeptides according to the invention. The invention also relates to a method for isolating polypeptides having α-H-α-amino acid amide racemase activity, for isolating nucleic acids encoding the same and for isolating microorganisms comprising polypeptides having α-H-α-amino acid amide racemase activity. The invention also relates to new microorganisms comprising polypeptides having α-H-α-amino acid amide racemase activity.

BACKGROUND ART

α-H-α-Amino acid amides are readily available compounds and are important precursors in the production of pharmaceuticals and of α-H-α-amino acids. For example, enantiomerically enriched α-H-α-amino acids can be obtained from mixtures of D- and L-α-H-α-amino acid amides with randomly chosen enantiomeric excess (ee) by enantioselective enzymatic hydrolysis of one of the enantiomers of the α-H-α-amino acid amide. In such a process for the preparation of enantiomerically enriched α-H-α-amino acids, simultaneous racemization of the α-H-α-amino acid amides would be of great advantage because then complete conversion of the α-H-α-amino acid amide into the desired optically active α-H-α-amino acid is possible. Also, in other processes racemization of α-H-α-amino acid amides is often desired. As enzymatic racemization is preferable over chemical racemization (mild reaction conditions, environmental benefits, etc.), many attempts have been made to identify microorganisms with α-H-α-amino acid amide racemase activity and to isolate polypeptides with α-H-α-amino acid amide racemase activity and genes encoding this activity.

DISCLOSURE OF THE INVENTION

For the purpose of the present invention, α-H-α-amino acid amide racemase activity is defined as the ability to catalyze the racemization of an enantiomerically enriched α-H-α-amino acid amide according to formula 1,

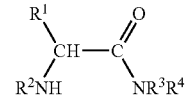

wherein $R^1$ stands for an optionally substituted alkyl of 1-20 C-atoms or an optionally substituted (hetero)aryl of 3-20 C-atoms (C-atoms of the substituents included) and wherein $R^2$, $R^3$ and $R^4$ each independently stand for H or an optionally substituted alkyl of 1-20 C-atoms or an optionally substituted (hetero)aryl of 3-20 C-atoms (C-atoms of the substituents included) and wherein $R^1$ may form a ring with $R^2$ and/or $R^3$ may form a ring with $R^4$ together with the carbon and/or nitrogen atoms to which they are bound. Each ring is preferably 5-8 membered. Preferably, $R^1$, $R^2$, $R^3$ or $R^4$ each independently stand for an alkyl of 1-10 C-atoms or a (hetero)aryl of 3-10 C-atoms (C-atoms of the substituents included). Substituents on the alkyl or (hetero) aryl may be chosen from the group of: hydroxy, alkoxy, mercapto, thioalkyl, alkyl, carboxy, amino, imino, nitro, halogen, carbamoyl, cyano, acyl, peroxy, sulpho or phospho. Examples of α-H-α-amino acid amides according to formula 1 are: proline amide, leucine amide, glutamic acid amide, phenylalanine amide, t-leucine amide, methionine amide, tryptophan amide, leucyl-glycine, valyl-glycine, valyl-alanine, leucyl-alanine.

With α-H-α-amino acid amide racemase is meant a polypeptide having α-H-α-amino acid amide racemase activity.

α-H-α-Amino acid amide racemase activity can be detected with methods similar to methods employed to determine racemizing activity of racemases acting on compounds other than α-H-α-amino acid amides. Such methods are known to the person skilled in the art. For example, by measuring the decrease in enantiomeric excess of an L-α-H-α-amino acid amide or of a D-α-H-α-amino acid amide, α-H-α-amino acid amide racemase activity can be determined.

In Fukumura, et al., *Agric. Biol. Chem.* (1977) 41:1509-1510, an α-amino-ε-caprolactam racemase isolated from *Achromobacter obae* is disclosed; the nucleic acid sequence coding for this enzyme and the amino acid sequence of this enzyme were published in Naoko, et al., *Biochemistry of vitamin B6* (1987) p. 449-452. For its enzymatic activity, the α-amino-ε-caprolactam racemase isolated from *Achromobacter obae* requires pyridoxal-5-phosphate as a cofactor (Ahmed, et al., *Agric. Biol. Chem.* (1983) 47:1887-1893).

The α-amino-ε-caprolactam racemase isolated from *Achromobacter obae* is known to exclusively catalyze the racemization of α-amino-ε-caprolactam. Although the α-amino-ε-caprolactam racemase from *Achromobacter obae* was tested for α-H-α-amino acid amide racemase activity with the following substrates, which are α-H-α-amino acid amides according to formula 1: L-tryptophan amide, L-leucine amide, L-leucyl-glycine, L-valyl-glycine, L-valyl-L-alanine, L-leucyl-L-alanine, no α-H-α-amino acid amide racemase activity was found even when an excess amount of enzyme was used (Ahmed, et al., *Agric. Biol. Chem.* (1983) 47:1887-1893).

EP-A-383403 discloses α-H-α-amino acid amide racemase activity in the genus *Klebsiella* and related genes and EP-B1-378592 discloses a α-H-α-amino acid amide racemase activity in *Arthrobacter* sp. ATCC 31652 (DSM 4639)

and in *Corynebacterium* sp. ATCC 31662 (DSM 4640). However, using the microorganisms disclosed in these publications, no racemization could be detected. Therefore, the documents EP-A-383403 and EP-B1-378592 should not be considered as prior art.

So, although much work has been done to find an α-H-α-amino acid amide racemase, up till now, not one α-H-α-amino acid amide racemase has been disclosed.

The invention now provides such α-H-α-amino acid amide racemases.

Applicants surprisingly also discovered a suitable method to isolated microorganisms displaying α-H-α-amino acid amide racemase activity, in which a microorganism containing sample is enriched by using D-α-amino-ε-caprolactam or a mixture of D- and L-α-amino-ε-caprolactam as a or as the sole nitrogen source and in which the thus found cultures are tested for α-H-α-amino acid amide racemase activity.

A suitable way for carrying out such a method is for example as follows; this method will be further referred to as the enrichment method. To find polypeptides according to the invention a microorganism containing sample, e.g., an environmental sample, for example a soil sample or a waste water sample is cultured in or on a suitable growth medium containing D-α-amino-ε-caprolactam or a mixture of D- and L-α-amino-ε-caprolactam as a or as the sole nitrogen source until growth can be detected.

The sample can be directly added onto/into the suitable growth medium with D-α-amino-ε-caprolactam or a mixture of D- and L-α-amino-ε-caprolactam as a or as the sole nitrogen source. There are also other ways of applying the sample to the medium, for example by adding the filtrate of a wash solution used to wash the sample with.

The culturing of the environmental sample in or on a suitable growth medium containing D-α-amino-ε-caprolactam or a mixture of D- and L-α-amino-ε-caprolactam as the sole nitrogen source is a so-called enrichment and was described by Fukumura, et al., *Agric. Biol. Chem.* (1977) 41:1321-1325, who used this enrichment in a method to isolate α-amino-ε-caprolactam racemases. Preferably, the enrichment is continued by one or more transfers of the cultured microorganism(s) into or onto a 'fresh' suitable growth medium containing D-α-amino-ε-caprolactam or a mixture of D- and L-α-amino-ε-caprolactam as the sole nitrogen source until a monoculture (as opposed to mixculture) is reached. Typically, this will be after 4 or 5 transfers.

It may be of advantage to add other nitrogen sources than D- or a mixture of D- and L-α-amino-ε-caprolactam, for example to help the cultures to start growing. For a good enrichment, however, the D-α-amino-ε-caprolactam or a mixture of D- and L-α-amino-ε-caprolactam is present in such amounts that microorganisms having the ability to convert D- and/or L-α-amino-ε-caprolactam, can continue to grow, whereas other microorganisms do not.

The person skilled in the art knows how to choose the culture conditions, for instance the conditions of the culture may depend on the source of the environmental sample and/or on the desired conditions of the desired process.

The microorganisms obtained by enrichment are tested for α-H-α-amino acid amide racemase activity. This testing for α-H-α-amino acid amide racemase activity can be done directly on the whole cells or on permeabilized cells of the colonies obtained after plating the cultured microorganisms. Alternatively, the colonies obtained are cultured separately in a suitable growth medium containing D-α-amino-ε-caprolactam or a mixture of D- and L-α-amino-ε-caprolactam as a or the sole nitrogen source, after which cell free extract is prepared therefrom, which is subsequently tested for α-H-α-amino acid amide racemase activity.

Cell free extract can be prepared according to standard methods known to the person skilled in the art, e.g., by sonification, French press, etc. Cell permeabilization can be obtained according to standard methods known to the person skilled in the art, e.g., by addition of small amounts of toluene. Suitable growth media are in fact all media, which contain as a or as the sole nitrogen source D-α-amino-ε-caprolactam or a mixture of D- and L-α-amino-ε-caprolactam. Suitable growth media are well known in the art. They can for example be composed by the person skilled in the art with guidance from Sambrook, J., et al., *Molecular Cloning: A Laboratory Manual*, 2nd ed., Cold Spring Harbor Laboratory, Cold Spring Harbor Laboratory Press, Cold Spring Harbor, N.Y., 1989.

Testing for α-H-α-amino acid amide racemase activity is preferably performed on a monoculture, but can also be performed on a mixculture.

In a preferred embodiment of the invention, the mix and/or monocultures obtained after the enrichment method, are tested for the ability to use L-α-amino-ε-caprolactam and for the ability to use D-α-amino-ε-caprolactam as a or as the sole nitrogen source.

Therefore, the invention also relates to a method for isolating microorganisms displaying α-H-α-amino acid amide racemase activity, comprising the steps of:

a) Culturing, in one or more transfer steps, a microorganisms containing sample in or on a suitable growth medium containing D-α-amino-ε-caprolactam or a mixture of D- and L-α-amino-ε-caprolactam as a or as the sole nitrogen source.

b) Testing the thus obtained microorganisms for α-H-α-amino acid amide racemase activity.

Surprisingly, it was found that the enrichment method is suitable for the isolation of microorganisms displaying α-H-α-amino acid amide racemase activity. This is the more surprising since this enrichment selects for α-amino-ε-caprolactam racemase activity and not for α-H-α-amino acid amide racemase activity. Therefore, the invention also relates to new microorganisms (comprising polypeptides) having α-H-α-amino acid amide racemase activity obtainable with said method.

Several microorganisms might be isolated this way, for example it may be possible to isolated microorganisms from the following genera: *Agrobacterium, Ochrobactrum, Arthrobacter, Micrococcus, Aureobacterium, Corynebacterium, Rhodococcus, Brevibacterium, Rubrobacter, Nocardioides, Terrabacter.*

Several monocultures of strains of microorganisms displaying α-H-α-amino acid amide racemase activity were isolated with the enrichment method and these microorganisms were deposited under the Budapest Treaty with The National Collections of Industrial and Marine Bacteria Limited (NCIMB), Aberdeen, Scotland, on May 8, 2002; *Agrobacterium rhizogenes* Na was deposited under number NCIMB 41127, *Agrobacterium rhizogenes* Bi was deposited under number NCIMB 41128, *Arthrobacter nicotianae* was deposited under number NCIMB 41126, *Ochrobactrum anthropi* 1A was deposited under number NCIMB 41129.

From isolated microorganisms obtained with the enrichment method it is possible to isolate a nucleic acid sequence encoding a polypeptide having α-H-α-amino acid amide racemase activity and to clone and express this nucleic acid to produce a polypeptide according to the invention. The isolation of a nucleic acid sequence and subsequent recloning and expression thereof can be done according to standard methods, which are known to the person skilled in the art.

Therefore, the invention also relates to a method for isolating a nucleic acid sequence encoding a polypeptide with α-H-α-amino acid amide racemase activity, comprising the steps of:

a) Culturing in one or more transfer steps, a microorganism containing sample in or on a suitable growth medium containing D-α-amino-ε-caprolactam or a mixture of D- and L-α-amino-ε-caprolactam as a or as the sole nitrogen source.

b) Testing the thus obtained microorganism(s) for α-H-α-amino acid amide racemase activity.

c) Isolating a nucleic acid sequence encoding an α-H-α-amino acid amide racemase from the obtained microorganism(s) in a manner known per se.

Isolating a nucleic acid sequence encoding a polypeptide having α-H-α-amino acid amide racemase activity from a microorganism having α-H-α-amino acid amide racemase activity can for example be done by preparing a DNA library, a cDNA library or an expression library from the microorganism(s) having α-H-α-amino acid amide racemase activity, by (partial) purification of the polypeptide having α-H-α-amino acid amide racemase activity followed by reversed genetics or by using nucleic acid arrays. These techniques are all known to the person skilled in the art. For example, after the preparation of a DNA or cDNA library, the nucleic acid encoding a polypeptide having α-H-α-amino acid amide racemase activity may be selected by using a probe or a PCR-primer based on sequence information of a homologous gene or on sequence information of a polypeptide having α-H-α-amino acid amide racemase activity. For example, after the preparation of an expression library, the clone of the library having α-H-α-amino acid amide racemase activity may be selected by using a α-H-α-amino acid amide racemase activity assay, by using the enrichment method of the invention or by using antibodies raised against a polypeptide having α-H-α-amino acid amide racemase activity. For example, reversed genetics can be performed by the purification and sequencing of (part of) the polypeptide having α-H-α-amino acid amide racemase activity and isolating the desired nucleic acid sequence based on the sequence information of the polypeptide having α-H-α-amino acid amide racemase activity, for example with a probe or a PCR-primer. For example, DNA arrays may be used to derive the nucleic acid sequence encoding a polypeptide having α-H-α-amino acid amide racemase activity, if the genomic sequence of the microorganism having α-H-α-amino acid amide racemase activity is known by comparing the expression pattern of the microorganism under conditions under which the microorganism does not display α-H-α-amino acid amide racemase activity to conditions under which the microorganism does display α-H-α-amino acid amide racemase activity.

In one embodiment of the invention, the nucleic acid sequence encoding an α-H-α-amino acid amide racemase is isolated as follows.

In a first step total DNA is isolated and a gene library is prepared from the microorganisms obtained by the enrichment method and expressed in a suitable vector in a suitable host (e.g., as described in the examples). In a second step, the clones of the gene library containing a vector with insert (the insert is a piece of DNA isolated from the microorganisms) are tested on the ability to catalyse the racemization of an α-H-α-amino acid amide. For example, testing of the clones for α-H-α-amino acid amide racemase activity can be done according to the methods as described in the examples.

In subsequent steps, the nucleic acid sequence of the insert of the vector in a clone having the ability to catalyse the racemization of an α-H-α-amino acid amide is determined and open reading frames are identified from the thus determined nucleic acid sequence, after which the open reading frames are recloned and expressed in a suitable vector and in a suitable host and again tested for α-H-α-amino acid amide racemase activity. By expression of the open reading frame encoding α-H-α-amino acid amide racemase activity in a suitable vector in a suitable host a polypeptide having α-H-α-amino acid amide racemase activity according to the invention can be produced.

With the enrichment method and subsequent isolation of the nucleic acid sequence, the nucleic acid sequence encoding an α-H-α-amino acid amide racemase from a strain identified as *Ochrobactrum anthropi* 1A deposited under number NCIMB 41129 with the NCIMB was obtained. This nucleic acid sequence is presented in SEQ ID NO: 1. The amino acid sequence of the corresponding polypeptide is presented in SEQ ID NO: 2. It was found that the α-H-α-amino acid amide racemase, with its amino acid sequence presented in SEQ ID NO: 2, is active over a broad pH and temperature range. With this enrichment method, also the nucleic acid sequence encoding an α-H-α-amino acid amide racemase from a strain identified as *Arthrobacter nicotianae* deposited under number NCIMB 41126 with the NCIMB was identified (SEQ ID NO:8). The amino acid sequence of the corresponding polypeptide is presented in SEQ ID NO:9.

The invention also relates to nucleic acid sequences encoding polypeptides with α-H α-amino acid amide racemase activity obtainable by the above method.

A nucleic acid sequence of encoding a polypeptide with α-H-α-amino acid amide racemase activity according to the invention, such as a nucleic acid sequence with the sequence of SEQ ID NO:1 or of SEQ ID NO:8 may also be isolated using standard molecular biology techniques and the sequence information provided herein. For example, using all or a portion of the nucleic acid sequence of SEQ ID NO:1 or SEQ ID NO:8 as a hybridization probe, a nucleic acid sequence according to the invention can be isolated using standard hybridization and cloning techniques (e.g., as described in Sambrook, J., et al., supra).

Moreover, a nucleic acid sequence encompassing all or a portion of SEQ ID NO:1 or SEQ ID NO:8 can be isolated by the polymerase chain reaction (PCR) using synthetic oligonucleotide primers designed based upon the sequence information contained in SEQ ID NO:1 or SEQ ID NO:2, respectively SEQ ID NO:8 or SEQ ID NO:9.

A nucleic acid sequence of the invention can be amplified using for example genomic DNA, cDNA or alternatively mRNA as a template and appropriate oligonucleotide primers according to standard (RT)-PCR amplification techniques. The nucleic acid so amplified can be cloned into a suitable vector and characterized by DNA sequence analysis.

Furthermore, oligonucleotides corresponding to or hybridizable to nucleic acid sequences according to the invention can be prepared by standard synthetic techniques, e.g., using an automated DNA synthesizer.

It should be noted that the invention also includes mutants of the nucleic acids encoding polypeptides having α-H-α-amino acid amide racemase activity, which have one or more mutations as compared to the corresponding polypeptide isolated from a naturally occurring host. Methods for making mutations are known to the person skilled in the art, e.g., by random mutagenesis (for example by error prone PCR or by UV radiation), site directed mutagenesis, etc.

The invention also relates to a method for producing a polypeptide with α-H-α-amino acid amide racemase activity, comprising the steps of:
a) Culturing in one or more transfer steps, a microorganism containing sample in or on a suitable growth medium containing D-α-amino-ε-caprolactam or a mixture of D- and L-α-amino-ε-caprolactam as a or as the sole nitrogen source.
b) Testing the thus obtained microorganisms for α-H-α-amino acid amide racemase activity.
c) Isolating a nucleic acid sequence encoding an α-H-α-amino acid amide racemase from the obtained microorganism(s) in a manner known per se.
d) Expressing the nucleic acid sequence in a suitable host to produce a polypeptide with α-H-α-amino acid amide racemase activity.

Expressing the nucleic acid sequence encoding a polypeptide according to the invention, can for example be done by cloning the nucleic acid in a suitable vector and after introduction in a suitable host, (over)expressing the sequence according to standard cloning and expression techniques, which are known to the person skilled in the art (e.g., as described in Sambrook, J., et al., supra), to produce a polypeptide according to the invention. Therefore, the invention also relates to vectors comprising a nucleic acid sequence according to the invention.

Alternatively, to produce a polypeptide according to the invention, the nucleic acid sequence encoding a polypeptide according to the invention can be integrated into the genome of a host cell and be (over)expressed. This can be done according to methods known to the person skilled in the art. Therefore, the invention also relates to a host cell comprising and expressing a nucleic acid sequence according to the invention, preferably to a host cell comprising a vector comprising a nucleic acid sequence according to the invention.

Alternatively, a polypeptide according to the invention can be overexpressed in its natural host, for example by placing a suitable promoter upstream of the nucleic acid sequence according to the invention, by integrating one or more copies of a nucleic acid sequence according to the invention into the genome of its natural host, preferably by expressing a nucleic acid according to the invention in a suitable vector in its natural host, which are all methods known to the person skilled in the art.

Suitable hosts are the hosts normally used for cloning and expression and are known to the person skilled in the art. Examples of suitable *E. coli* host strains are: Top10F', TOP10, DH10B, DH5α, HB101, W3110, BL21(DE3) and BL21(DE3)pLysS.

Suitable vectors are the vectors normally used for cloning and expression and are known to the person skilled in the art. Examples of suitable vectors for expression in *E. coli* are given, e.g., in Table 1 in Makrides, S. C., *Microbiological Reviews* (1996) p. 512-538. Preferably, the vector contains a promoter upstream of the cloning site containing the nucleic acid sequence encoding the polypeptide with α-H-α-amino acid amide racemase activity, which can be switched on after the host has been grown to express the corresponding polypeptide having α-H-α-amino acid amide racemase activity. Promoters, which can be switched on and off are known to the person skilled in the art and are for example the lac promoter, the araBAD promoter, the T7 promoter, the trc promoter, the tac promoter, the trp promoter, and the aroH promoter.

The invention therefore relates to polypeptides with α-H-α-amino acid amide racemase activity obtainable by the above method.

In a preferred embodiment of the invention, the invention relates to isolated polypeptides having α-H-α-amino acid amide racemase activity and having a degree of identity with the amino acid sequence presented in SEQ ID NO:2 of at least about 35%, preferably of at least about 40%, more preferably of at least about 50%, even more preferably of at least about 55%, in particular of at least about 65%, more in particular of at least about 75%, even more in particular of at least about 85%, even more in particular of at least about 90%, even more in particular of at least about 95%, most in particular of at least about 97%.

In another preferred embodiment of the invention, the invention relates to isolated polypeptides having α-H-α-amino acid amide racemase activity and having a degree of identity with the amino acid sequence presented in SEQ ID NO:9 of at least about 50%, preferably of at least about 60%, more preferably of at least about 70%, even more preferably of at least about 80%, in particular of at least about 90%, more in particular of at least about 95%, most in particular of at least about 97%.

For purpose of the present invention, the degree of identity between two amino acid sequences is determined by the blastp pairwise alignment algorithm (NCBI), with an identity table and the following alignment parameters: mismatch=−3 penalty=−3, gap extend=1, match bonus=1, Gap x−droff=50, expect=10, wordsize=3.

The present invention also relates to isolated polypeptides having α-H-α-amino acid amide racemase activity, which are encoded by nucleic acid sequences which hybridize under low stringency conditions, preferably under medium stringency conditions, more preferably under high stringency conditions and most preferably under very high stringency conditions with the coding sequence of SEQ ID NO:1 or a complementary strand thereof or with the coding sequence of SEQ ID NO:8 or a complementary strand thereof.

Hybridization experiments can be performed by a variety of methods, which are well available to the skilled man. General guidelines for choosing among these various methods can be found in, e.g., chapter 9 of Sambrook, J., et al., supra.

With stringency of the hybridization conditions is meant, the conditions under which the hybridization, consisting of the actual hybridization and wash steps, are performed. Wash steps are used to wash off the nucleic acids, which do not hybridize with the target nucleic acid immobilized on for example a nitrocellulose filter. The stringency of the hybridization conditions can for example be changed by changing the salt concentration of the wash solution and/or by changing the temperature under which the wash step is performed (wash temperature). Stringency of the hybridization increases by lowering the salt concentration in the wash solution or by raising the wash temperature. For purpose of this application, the hybridization is performed in 6× sodium chloride/sodium citrate (SSC) at about 45° C. for about 12 hours. Two consecutive 30 minutes wash steps in 1×SSC, 0.1% SDS at 50° C. is an example of low stringency, at 55° C. an example of medium stringency, at 60° C. an example of high stringency, at 65° C. an example of very high stringency.

The present invention also relates to isolated polypeptides having α-H-α-amino acid amide racemase activity and which display immunological cross-reactivity with an antibody raised against a fragment of the amino acid sequence according to SEQ ID NO:2 or SEQ ID NO:9.

The immunological cross reactivity may be assayed using an antibody raised against, or reactive with, at least one epitope of the isolated polypeptide according to the present invention having α-H-α-amino acid amide racemase activity. The antibody, which may either be monoclonal or polyclonal, may be produced by methods known in the art, e.g., as described by Hudson, et al., *Practical Immunology*, Third Edition (1989), Blackwell Scientific Publications. The immunochemical cross-reactivity may be determined using assays known in the art, an example of which is Western blotting, e.g., as described in Hudson, et al., supra.

The invention also relates to fragments of the polypeptides according to the invention and having α-H-α-amino acid amide racemase activity of at least 100 amino acids, preferably of 125 to 350 amino acids, more preferably of 200 to 300 amino acids.

The invention also relates to fusion proteins made by expression of a nucleic acid sequence encoding a polypeptide according to the invention operatively linked to one or more nucleic acid sequences, which encode (a) marker polypeptide(s). With operatively linked is meant, that the nucleic acid sequences are linked such that, if expressed, the polypeptide according to the invention with the marker polypeptide(s) on its N- and/or C-terminus is produced. The marker polypeptide can serve many purposes, for example, it may be used to increase the stability or the solubility of the fusion protein, it may be used as a secretion signal, which is a signal that directs the fusion protein to a certain compartment in the cell or it may be used to facilitate purification of the fusion protein. An example of a marker polypeptide used to facilitate purification of the fusion protein is the hexahistidine peptide. The purification of a fusion protein with a hexahistidine tag is for example described in Gentz, et al., *Proc. Natl. Acad. Sci. USA* (1989) 86:821-824. A fusion protein with a hexahistidine tag can for example be produced in a pQE vector (Qiagen, Inc.), by following the protocol of the supplier.

The invention also relates to nucleic acid sequences encoding polypeptides having α-H-α-amino acid amide racemase activity according to the invention. These nucleic acid sequences may be obtained with the enrichment method and subsequent isolation of the desired nucleic acid as described above.

α-H-α-amino acid amide racemases and microorganisms displaying α-H-α-amino acid amide racemase activity according to the invention can be used in a process for the racemization of an enantiomerically enriched α-H-α-amino acid amide. Therefore, the invention relates to a process for the racemization of an enantiomerically enriched α-H-α-amino acid amide, wherein the racemization is performed in the presence of a polypeptide according to the invention or a microorganism according to the invention.

α-H-α-Amino acid amide racemases according to the invention can suitably be used together with an enantioselective amidase in a process for the preparation of enantiomerically enriched α-H-α-amino acids from a mixture of D- and L-α-H-α-amino acids amides or in a process for the preparation of L-α-H-α-amino acids from the corresponding D-α-H-α-amino acid amides or in a process for the preparation of D-α-H-α-amino acids from the corresponding L-α-H-α-amino acid amides. Use of α-H-α-amino acid amide racemases in such processes will (theoretically) lead to a 100% conversion of the α-H-α-amino acid amide into the corresponding enantiomerically enriched α-H-α-amino acid (100% yield). The invention therefore also relates to the use of an α-H-α-amino acid amide racemase according to the invention in combination with an enantioselective amidase in a process for the preparation of enantiomerically enriched α-H-α-amino acids from a mixture of D- and L-α-H-α-amino acids amides or in a process for the preparation of L-α-H-α-amino acids from the corresponding D-α-H-α-amino acid amides or in a process for the preparation of D-α-H-α-amino acids from the corresponding L-α-H-α-amino acid amides. The invention also relates to a process for the preparation of an enantiomerically enriched α-H-α-amino acid from a mixture of the corresponding D- and L-α-H-α-amino acid amides or the preparation of an L-α-H-α-amino acid from the corresponding D-α-H-α-amino acid amide or the preparation of a D-α-H-α-amino acid from the corresponding L-α-H-α-amino acid amide, wherein the process is performed in the presence of an enantioselective amidase and a polypeptide with α-H-α-amino acid amide racemase activity according to the invention or a microorganisms displaying α-H-α-amino acid amide racemase activity according to the invention.

Preferably, in the above-mentioned processes, the enantioselective amidase is at least 90% enantioselective, more preferably at least 95% enantioselective, even more preferably at least 98% enantioselective, most preferably at least 99% enantioselective. 90% Enantio-selectivity of the amidase (for example a D-amidase) is defined for the present invention as the ability of the amidase to convert a racemic mixture of DL-α-H-α-amino acid amides into 90% of one enantiomer of the α-amino acid (e.g., D-α-H-α-amino acid) and into 10% of the other enantiomer of the α-H-α-amino acid (e.g., L-α-H-α-amino acid) at 50% total conversion of the α-H-α-amino acid amide mixture. 95% Enantio-selectivity (e.g., 95% D- and 5% L-α-H-α-amino acid) corresponds to an E-value of 58.4 (e.e. 90%). 98% Enantio-selectivity (e.g., 98% D- and 2% L-α-H-α-amino acid) corresponds to an E-value of 193.6 (e.e. 96%). 99% Enantio-selectivity (e.g., 99% D- and 1% L-α-H-α-amino acid) corresponds to an E-value of 458.2 (e.e. 98%).

For α-H-α-amino acid amide racemase activity, it may sometimes be of advantage to add a cofactor, for example pyridoxal-5-phosphate.

Preferably, in said processes, the α-H-α-amino acid amide racemase according to the invention does not display α-H-α-amino acid racemase activity, i.e., the ability to catalyse the racemization of a D-α-H-α-amino acid and an L-α-H-α-amino acid.

The invention is illustrated by way of the following examples. However, these examples are not meant to restrict the invention.

EXAMPLES

General Procedures

Standard molecular cloning techniques such as plasmid DNA isolation, gel electrophoresis, enzymatic restriction modification of nucleic acids, *E. coli* transformation etc. were performed as described by Sambrook, et al., supra, or the supplier's manual. Standard molecular cloning enzymes such as restriction endonucleases, T4 DNA ligase, etc., were obtained from Invitrogen (Breda, The Netherlands) unless otherwise stated. Synthetic oligodeoxynucleotides were obtained from Sigma-Genosys (Cambridge, UK), and Invitrogen (Paisley, Scotland, UK). DNA sequence analyses were performed by BaseClear (Leiden, The Netherlands) using the chain termination method with dye-labeled dideoxy-terminators.

Example 1

Enrichment Method

In this enrichment procedure, different soil and sludge samples that had been stored at −80° C., were used for direct inoculation of 50 ml of liquid Medium A (Yeast Carbon Base (Difco, 11.7 g/l), $KH_2PO_4$ (6.7 g/l), $K_2HPO_4$ (8.9 g/l), pH 7.0), containing racemic DL-α-amino-ε-caprolactam (2 g/l) as sole nitrogen source. Per flask, one spatula of inoculum was used. The different flasks were incubated at 28° C. and 200 rpm.

After about 2 days good growth was observed in all flasks. After sedimentation of the soil particles in all cultures, 1:1,500 dilutions were prepared in Medium A containing 2 g/l DL-α-amino-ε-caprolactam, and were incubated at 28° C. and 200 rpm. After obtaining sufficient growth, samples were taken from each flask to determine the concentration of both L- and D-α-amino-ε-caprolactam in the culture broths. These samples were centrifuged and the supernatants were filtered through a 0.45 μM filter to remove all cells. Then these samples were analyzed by HPLC. o-Phthaldehyde in combination with D-3-mercapto-2-methylpropionic acid was used in this HPLC method as a chiral reagent for the separation of both α-amino-ε-caprolactam enantiomers (Duchateau, et al., *J. Chromatogr.* (1992) 623:237-245).

Only flasks in which cultures had grown that used both enantiomers of α-amino-ε-caprolactam were selected for the next steps. Different dilutions of these cultures were plated onto plates with Medium A containing 2 g/l DL-α-amino-ε-caprolactam as sole nitrogen source, and were incubated at 28° C. Colonies were randomly chosen and re-isolated on the same type of selective plates to obtain monocultures. Then, a colony of each monoculture was transferred into 5 ml of Medium A containing 2 g/l DL-α-amino-ε-caprolactam. After 3 days of incubation at 28° C. and 200 rpm, the cultures obtained were analyzed for use of D- and L-α-amino-ε-caprolactam exactly as described above. The monocultures that could use both D- and L-α-amino-ε-caprolactam were stored at −80° C. in 20% (v/v) glycerol.

Cells from these monocultures were finally tested for α-amino-ε-caprolactam racemase activity. After cultivation in Medium A containing DL-α-amino-ε-caprolactam (2 g/l) at 28° C. and 200 rpm for three days, cells were harvested by centrifugation, washed with 20 mM HEPES-NaOH buffer (pH 7.7) and lyophilized.

Then 100 mg of these lyophilized cells from each monoculture were added to a reaction mixture consisting of 10 mM HEPES-NaOH buffer (pH 7.7), toluene (2,5 v/v %), pyridoxal-5-phosphate (20 μM), and L-α-amino-ε-caprolactam (2.5 m %). Chemical blanks (with the assay mixture without the lyophilized cells) were used as a negative control. All reaction mixtures (including the blanks) were incubated for approximately 72 hours at 40° C. before the reaction was stopped by the addition of 9 volumes of 1 M $H_3PO_4$. After removal of the cells by filtration through a 0.45 μM filter, these reaction mixtures were analyzed by the HPLC method described above to determine the concentration of D- and L-α-amino-ε-caprolactam. Finally, monocultures that formed D-α-amino-ε-caprolactam from the L-α-amino-ε-caprolactam substrate were sent to the NCIMB for strain determination. Nb. no D-α-amino-ε-caprolactam could be determined in the chemical blanks.

Strain Determination

One of the thus obtained monocultures that could racemize L-α-amino-ε-caprolactam was identified as an *Ochrobactrum anthropi* strain by the NCIMB and was deposited under the Budapest Treaty as *Ochrobactrum anthropi* IA with the NCIMB under number NCIMB 41129. The results of the determination are presented in Table 1.

TABLE 1

Results of strain identification of isolate IA by National Collections of Industrial and Marine Bacteria Limited (NCIMB LTD). Identification number ID4036.

| Isolate code | IA |
| --- | --- |
| Incubation temperature (° C.) | 30 |
| Gram stain | − |
| Spores | − |
| Motility | + |
| Colony morphology (after 2 days growth on LB medium) | Round, regular, entire, smooth, shiny, low convex, buff, opaque. 1 mm diameter. |
| Growth at 37° C. | + |
| Growth at 45° C. | − |
| Catalase | + |
| Oxidase | + |
| Fermentative in glucose OF | Oxidative |
| Results from API 20NE test: | |
| $NO_3$ reduction | + |
| Indole reduction | − |
| Acid from glucose | − |
| Arginine dihydroxylase | − |
| Urease | + |
| Aesculin hydrolysis | − |
| Gelatin hydrolysis | − |
| β-galactosidase | − |
| Glucose assimilation | + |
| Arabinose assimilation | + |
| Mannose assimilation | + |
| Mannitol assimilation | + |
| N-acetyl-glucosamine assimilation | + |
| Maltose assimilation | − |
| Gluconate assimilation | − |
| Caprate assimilation | − |
| Adipate assimilation | − |
| Malate assimilation | + |
| Citrate assimilation | + |
| Phenylacetate assimilation | − |
| Cytochrome oxidase | + |
| Results from further biochemical tests: | |
| Acid production in: | |
| Glucose ASS[a] | + |
| Dulcitol ASS | + |
| Adonitol ASS | + |
| Raffinose ASS | − |
| Xylose OF | + |
| Glycine CSU[b] | + |
| Nitrite reduction to $N_2$ | + |
| PPA | + |
| Simmons citrate | − |
| Tween 80 hydrolysis | − |
| Tyrosine decomposition | − |
| $H_2S$ production (PbAc) | + |

[a]ASS, ammonia salt sugar.
[b]CSU, carbon source utilization.

Measurement of α-H-α-amino Acid Amide Racemase Activity of Lyophilized *Ochrobactrum anthropi* IA Cells

*O. anthropi* IA cells were cultivated in Medium A containing DL-α-amino-ε-caprolactam (2 g/l) as sole nitrogen source. After incubation at 28° C. and 200 rpm for three days ($OD_{620\ nm}$=4.7), cells were harvested by centrifugation, washed in 20 mM HEPES-NaOH buffer of pH 7.7 and lyophilized.

The lyophilized cells were used to demonstrate α-H-α-amino acid amide racemase activity. The assay mixture consisted of 10 mM HEPES-NaOH buffer (pH 7.7) containing toluene (2,5 v/v %), pyridoxal-5-phosphate (20 μM), D- or L-leucine amide (2.5 m %) and in some cases EDTA (20 mM). Per assay 150 mg of lyophilized cells were used. Chemical blanks (with the assay mixture without the *O. anthropi* IA cells) were used as a negative control. All reaction mixtures (including the blanks) were incubated for approximately 72 hours at 40° C. before the reaction was stopped by the addition of 9 volumes of 1 M $H_3PO_4$. Finally, the reaction mixtures were analyzed by HPLC to determine the concentrations of D- and L-leucine amide and of D- and L-leucine. o-Phthaldehyde in combination with D-3-mercapto-2-methylpropionic acid was used in this HPLC method as a chiral reagent for the enantioseparation of these amino compounds (Duchateau, et al., *J. Chromatogr.* (1992) 623:237-245).

In a number of reactions EDTA was added to inhibit L- and/or D-specific amidase(s) present in the *O. anthropi* IA cells. By inhibiting this amidase, the L- and/or D-amino acid amide is not or just partly converted into the corresponding amino acid thereby enabling the demonstration of amino acid amide racemase activity by the detection of the other amino acid amide enantiomer. These reactions with EDTA (No. 3 & 4), clearly showed that *O. anthropi* IA cells contain an α-H-α-amino acid amide racemase activity, because D-leucine amide was converted into L-leucine amide and vice versa. The chemical blanks did not show this racemization reaction.

Without EDTA, amidases convert the substrate and/or product α-H-α-amino acid amides into α-H-α-amino acids thereby preventing direct detection of the other α-H-α-amino acid amide enantiomer as racemization product. Starting from D-leucine amide, however, the reaction without EDTA also clearly proved the presence of an α-H-α-amino acid amide racemase activity in *O. anthropi* IA, because this substrate was converted to significant amounts of L-leucine, and a control experiment excluded its formation via D-leucine, because *O. anthropi* IA did not racemize leucine. Formation of L-leucine from D-leucine amide could not be detected in the chemical blank.

TABLE 2

α-H-α-amino acid amide racemase activity in lyophilized *O. anthropi* IA cells.

| No. | Substrate | EDTA (20 mM) | D-leucine amide (m %) | L-leucine amide (m %) | D-leucine (m %) | L-leucine (m %) |
|---|---|---|---|---|---|---|
| 1 | D-leucine amide | − | 0.22 | <0.001 | 0.015 | 0.044 |
| 2 | L-leucine amide | − | <0.001 | <0.001 | 0.001 | 0.21 |
| 3 | D-leucine amide | + | 0.24 | 0.032 | 0.007 | 0.008 |
| 4 | L-leucine amide | + | 0.021 | 0.15 | 0.003 | 0.058 |

The concentrations given are the concentrations measured in the reaction mixtures, which are 10 times diluted as compared to the initial reaction mixtures.

Example 2

Enrichment Method

Approximately 30 g of fresh soil samples from different locations were resuspended in 50 ml of Medium A, supplemented with 2 g/l D-α-amino-ε-caprolactam as sole nitrogen source, and shaken for 30 minutes at 4° C. and 200 rpm. The suspensions were filtered through a filter paper to remove the soil particles. With the filtrates obtained the following two different approaches were used to select for strains that could use D-α-amino-ε-caprolactam as nitrogen source:

5 ml Of the different filtrates were transferred to empty 100 ml flasks. All flasks were incubated at 28° C. and 200 rpm until an $OD_{600\,nm}$ was reached of approximately 2.5. Then the cultures were diluted 1:100 in fresh Medium A containing 2 g/l D-α-amino-ε-caprolactam, again followed by a cultivation step. These dilution and recultivation step was repeated 3 more times. Then different dilutions of good growing cultures were plated onto plates with Medium A containing 2 g/l D-α-amino-ε-caprolactam as sole nitrogen source, that were incubated at 28° C. Colonies were randomly chosen and reisolated 5 times onto identical selective plates, yielding pure monocultures. Finally, these monocultures were stored at −80° C. in 20% (v/v) glycerol.

As alternative enrichment strategy, different dilutions of all filtrates were plated directly onto Medium A containing 2 g/l D-α-amino-ε-caprolactam as sole nitrogen source. After 2 days of incubation at 28° C., first colonies appeared on almost all plates. After a few more days to 3 weeks, a lot of morphologically different colonies were obtained. Morphologically different colonies were randomly chosen and reisolated 5 times onto identical selective plates, yielding pure monocultures. Finally, these monocultures were stored at −80° C. in 20% (v/v) glycerol.

Cells from these monocultures were finally tested for α-amino-ε-caprolactam racemase activity. After cultivation in 800 ml of Medium A containing 2 g/l of D-α-amino-ε-caprolactam at 28° C. and 200 rpm, cells were harvested by centrifugation (20 min. at 5,000×g, 4° C.), and resuspended in 40 ml of sonification buffer (NaCl, 16 g/l; KCl, 0.74 g/l; $Na_2HPO_4$, 0.27 g/l; glucose, 2 g/l; HEPES, 10 g/l, pH 7.0). Then the cells were disintegrated by sonification using a Soniprep 150 of MSE at an amplitude of 20 microns in cycles of 10 min. using time intervals of 10 sec. (i.e., 10 sec. sonification, 10 sec. cooling) and cooling in ice/acetone. After each cycle, the cells were viewed microscopically and the sonification procedure was stopped when 50-70% of the cells were broken.

Then D-α-amino-ε-caprolactam and pyridoxal-5-phosphate were added to the disintegrated cell suspensions of each monoculture to concentrations of 5 g/l and 0.01 mM respectively. After 1.5 h of incubation at 20° C. and 20 rpm, 2 ml samples were transferred into 1 ml of 1 M $H_3PO_4$. After removal of all particulates by centrifugation followed by filtration through a 0.22 μM filter, concentrations D- and L-α-amino-ε-caprolactam in the samples were determined by HPLC using the protocol as described in Example 1. Finally, monocultures that formed L-α-amino-ε-caprolactam from the D-α-amino-ε-caprolactam substrate were sent to the NCIMB for strain determination.

Strain Determination

The thus obtained monocultures were identified by the NCIMB as *Agrobacterium rhizogenes* (*Agrobacterium rhizogenes* Bi and *Agrobacterium rhizogenes* Na and *Arthrobacter nicotianae* via 16S rDNA sequence determination. The results of this 16S rDNA determination are presented below. The microorganisms were deposited under the Budapest Treaty with the NCIMB. *Agrobacterium rhizogenes* Na was deposited under number NCIMB 41127, *Agrobacterium rhizogenes* Bi under number NCIMB 41128 and *Arthrobacter nicotianae* under number NCIMB 41126.

Analysis of 16S rDNA Sequence

Methods

DNA extraction: The DNA was extracted using the Prepman purification kit and stored on ice until use.

Polymerase chain reaction: The 16S ribosomal DNA gene was amplified using universal eubacterial primers and analysed by electrophoresis on a 1% agarose gel.

DNA clean-up: The 500 bp fragment was purified by spin column centrifugation and resuspended in sterile distilled water.

DNA sequencing: The purified DNA product was automatically sequenced using the dideoxy chain terminator method (Sanger, et al., 1997).

Sequence analysis by database comparison: The sequence of the 16S rDNA gene was compared with nucleic acid sequence databases.

Results

The 16S rDNA sequences of *Agrobacterium rhizogenes* Na NCIMB 41127 (SEQ ID NO:5), *Agrobacterium rhizogenes* Bi NCIMB 41128 (SEQ ID NO:4), and *Arthrobacter nicotianae* NCIMB 41126 (SEQ ID NO:3) are presented in the sequence listing part.

Measurement of α-H-α-amino Acid Amide Racemase Activity of Disintegrated Cells of *Agrobacterium rhizogenes* Na, *Agrobacterium rhizogenes* Bi, *Arthrobacter nicotianae*

Preparation of Disintegrated Cells

After growth of these three strains in Medium A containing 2 g/l of D-α-amino-ε-caprolactam, cells were harvested by centrifugation at 12,000×g. After centrifugation the supernatant was decanted and the wet weight of the pellet was measured. To the pellet, sonification buffer (NaCl, 16 g/l; KCl, 0.74 g/l; $Na_2HPO_4$, 0.27 g/l; glucose, 2 g/l; HEPES, 10 g/l, pH 7.0) was added in a 1:2 ratio (wet weight cell pellet:ml buffer). During storage between cell harvest and sonification the pellet was frozen in the sonification buffer at −86° C.

Sonification was performed with a Soniprep 150 of MSE at maximal amplitude of 20 microns in periods of 10 min. using time intervals of 10 sec. (i.e., 10 sec. sonification, 10 sec. cooling down), cooling the sample on ice/acetone. Each 10 min. the cells were viewed microscopically. The sonification procedure was stopped when >70% of the cells were broken.

α-H-α-Amino Acid Amide Racemase Activity Test with Disintegrated Cells 1 ml Of disintegrated cells of each of the three strains was incubated in a HEPES-NaOH buffer (20 mM) pH 7.7, to which pyridoxal-5-phosphate (0.01 mM) was added as a cofactor and D-leucine amide (60.8 mM) as a substrate in a total volume of 10 ml (0.79 w/w % D-leucine amide). After 0 and 139 hours 1 ml samples were taken (of which the exact weight was measured) and the reaction in these samples was stopped by adding 1 ml methanol (of which the exact weight was measured too; to be able to calculate dilution factors). Stopped reaction mixtures were centrifuged to remove particulates. The supernatants were frozen at −86° C. until HPLC analysis according to the method given in Example 1.

Blank reaction mixtures were prepared, sampled and stopped in the same way, with the exception that no substrate was added and that instead of disintegrated cells, only HEPES-NaOH buffer (20 mM, pH 7.7) was added.

The results are shown in Table 3.

TABLE 3

Measurement of α-H-α-amino acid amide racemase activity of disintegrated cells of *Agrobacterium rhizogenes* Na, *Agrobacterium rhizogenes* Bi and *Arthrobacter nicotianae*.

| Sample code | Incubation time (h) | D-leucine (w/w %) | L-leucine (w/w %) | D-leucine amide (w/w %) |
|---|---|---|---|---|
| *A. nicotianae* | 139 | 0.002 | 0.068 | 0.56 |
| *A. rhizogenes* Na | 139 | 0.036 | 0.078 | 0.51 |
| *A. rhizogenes* Bi | 139 | 0.013 | 0.025 | 0.61 |

From the table it can be seen that α-H-α-amino acid amide racemase activity is present in the disintegrated cells of *Agrobacterium rhizogenes* Na, *Agrobacterium rhizogenes* Bi and *Arthrobacter nicotianae* as D-leucine amide is converted into L-leucine; this conversion is not detected in the chemical blanks. In the chemical blanks no D-leucine or L-leucine could be detected even after 139 hours; the D-leucine amide concentration was constant (0.7 w/w %) meaning that D-leucine amide is very stable under the applied reaction conditions.

Example 3

Isolation of the α-H-α-amino Acid Amide Racemase Gene from *Ochrobactrum anthropi* IA Expression Library Construction To obtain single colonies, a glycerol stock of *O. anthropi* IA was streaked onto a yeast carbon base plate containing 0.5% (w/v) DL-α-amino-ε-caprolactam as single nitrogen source, and cultivated at 28° C. A single colony was transferred to 150 ml of LB liquid medium, and grown at 28° C. with vigorous shaking to an $OD_{620\ nm}$ of 0.9. Then cells were harvested by centrifugation and frozen at −20° C.

After thawing the cells, total DNA was isolated according to the Qiagen Genomic DNA Purification Procedure for bacteria using Qiagen Genomic-tip 100/G tips. The standard Qiagen protocol was followed with the following modifications:

The first incubation step to effect cell lysis was performed without proteinase K for 2 h at 37° C., whereafter twice the suggested amount of proteinase K was added and the solution was incubated for another 2 h at 50° C.

Before application of the lysate to the Qiagen tips, a centrifugation step (10 min. at 5,000×g, 4° C.) was applied to pellet the particulate matter.

The lysate from the cells of the 150 ml culture was applied to 3 G/100 columns.

50 μg of the obtained chromosomal DNA was then partially digested with Sau3A I at 1/12 U per μg DNA for 30 minutes. Half of the digested DNA was run on a 0.6% agarose gel and DNA fragments between 4 and 10 kb in size were isolated and redissolved in 20 μl of 10 mM Tris-HCl, pH 8.0 buffer.

Vector DNA was prepared by the digestion of 1 μg of pZErO-2 (Invitrogen, Groningen, The Netherlands) with BamH I according to the protocol of Invitrogen.

Linearized vector DNA (50 ng) and *O. anthropi* IA chromosomal DNA fragments (10 μl) were ligated with T4 DNA ligase (according to the protocol of Invitrogen). Subsequently, the ligation mixture was precipitated with NaAc/ ethanol and resuspended in 20 µl TE-buffer. 1 µl of this solution was used for the electroporation of electrocompetent *E. coli* DH10B cells (Life Technologies) using a BioRad gene pulser (conditions: 2.5 kV, 25 µF, 100 Ω, 0.1 cm cuvette, 40 µl cell suspension) according to the protocol of the supplier. Transformants were plated onto LB medium with 50 mg/l kanamycin and incubated at 28° C. for 24 h. In total over 12,000 colonies were obtained which formed the primary gene library. All 12,000 colonies were pooled in LB medium supplemented with 50 mg/l kanamycin. Part of the cell suspension obtained was used for a total plasmid isolation according to the QiaPrep procedure (Qiagen). This "library in plasmid form" was stored at −20° C. till further use. To the remaining part of the cell suspension, glycerol was added to a final concentration of 20% (v/v). The resulting suspension was stored in aliquots at −80° C. as primary gene library.

Preparation of L-aminopeptidase Help Solution

The L-aminopeptidase help solution for the α-H-α-amino acid amide racemase screening procedure was prepared from a recombinant *E. coli* strain containing plasmid pTrcLAP. The *E. coli* expression vector pTrcLAP contains the *Pseudomonas putida* ATCC 12633 pepA gene under the control of the trc promoter. Detailed information on this *P. putida* L-aminopeptidase encoding gene can be found in Sonke, T., et al., *Stereoselective Biocatalysis* (2000) (Ed.: R. N. Patel) Dekker, New York, pp. 23-58.

A fresh overnight culture of *E. coli* TOP10/pTrcLAP was used to inoculate 200 ml of LB medium containing both 0.4 mM of IPTG and 100 mg/l of ampicillin. After overnight growth at 30° C., cells were pelleted by centrifugation and resuspended in 4 ml of 50 mM Tris-HCl, pH 7.5. After cell disruption by one passage through a french press (pressure of 140 Mpa in a 4 ml french press cell), solid particles were collected by centrifugation (45 min. at 40,000×g, 4° C.). The pellet was resuspended in 2 ml of Tris-HCl, pH 7.5 containing 100 mM of $MgSO_4$. This suspension was gently stirred for 30 min. at 4° C. After removal of the particles via centrifugation (45 min. at 40,000×g, 4° C.), the clear solution was stored in aliquots at −20° C. for use in the screening assay.

Screening

The "library in plasmid form" solution was diluted 1,000 times in water. 1 µl of this plasmid solution was used to transform electrocompetent *E. coli* TOP10 cells (Invitrogen), and the transformants were plated onto LB medium with 50 mg/l kanamycin. After 2 days of incubation at 28-30° C. the obtained colonies were large enough to be transferred to 200 µl of liquid screening medium (tryptone 16 g/l; yeast extract 3 g/l; NaCl 5 g/l; glycerol 2 g/l; pH 7.3) with 50 mg/l kanamycin in microtiter plates. The cultures were grown for 2 days at 28-30° C. Next, a replica of the microtiter plates was prepared by the transfer of a few microliter of each well to new microtiter plates containing solid (0.8% agar) LB medium with 50 mg/l kanamycin. These plates were incubated at 28-30° C. for 16-20 h, after which they were stored at 4° C. as masterplates. The cells from the remaining part of the cell suspensions were harvested by centrifugation (10 min. at 1,500×g, room temperature), washed twice with 50 mM Tris-HCl buffer, pH 7.5, and finally re-suspended in 50 µl of 50 mM Tris-HCl buffer, pH 7.5.

The screening reaction was started by the addition of 50 µl of substrate solution containing a mixture of 140 mM D-phenylalanine amide, D-leucine amide and D-valine amide each in 50 mM Tris-HCl, pH 7.5 and 2 mM $MnCl_2$. After 20 h incubation of the microtiterplates on a shaker at 30° C., 2 µl of L-aminopeptidase help solution (for preparation see earlier section) was added. After an additional 1.5 h incubation at 30° C., all reactions were stopped by the addition of 100 µl of 0.15 M HCl.

Subsequently, the ammonium concentration in all reaction mixtures was determined by transfer of 7 µl of these mixtures to new microtiter plates containing 93 µl of GDH reagent per well. This GDH reagent contained per 100 ml 43 mg of NADH, 116 mg of α-ketoglutaric acid, 11.8 mg of ADP and 1200 U of glutamate dehydrogenase (Sigma) in 150 mM Tris-HCl, pH 8.0. After 15 min. incubation at 37° C. the OD340 nm in each well was measured using a Spectramax plus microtiter plate reader (Molecular Devices, Sunnyvale, Calif., USA). Clones that showed an $OD_{340\ nm}$ that was lower than the mean value of the microtiter plate containing this clone decreased with three times the standard deviation of that same microliter plate, were regarded as potential positive clones.

Of 11,272 clones screened, 32 clones could be identified as potential positive clones.

Confirmation of Potential Positive Clones

Of all 32 potential positive clones identified in the screening, material from the masterplates was used to inoculate 3 ml of liquid screening medium containing 50 mg/l kanamycin. After growth for 2 days at 30° C., cells were collected by centrifuging 2 ml of these cell cultures. Then the cell pellets were washed four times in 25 mM Tris-HCl buffer, pH 7.5. Subsequently, the cell pellets were resuspended in 100 µl substrate solution containing 70 mM of D-phenylalanine amide, or D-leucine amide, or D-valine amide in 50 mM Tris-HCl, pH 7.5 and 1 mM $MnCl_2$. After incubation for 20 h at 30° C., the reactions were stopped by the addition of 100 µl of 0.15 M HCl, after which the reaction mixtures were analyzed by the HPLC method described in Example 1.

Of the 32 potential positive clones identified in the screening, one showed significant formation of L-leucine from D-leucine amide. This clone contained the *O. anthropi* IA α-H-α-amino acid amide racemase gene on its 7.7 kb plasmid. This was concluded from the fact that transformation of this plasmid into *E. coli* TOP10 cells inevitably led to recombinant cells that converted D-leucine amide into L-Leucine. Sequencing of this plasmid, that was named pOa(1)PLV49B10, revealed the complete nucleotide sequence of the α-H-α-amino acid amide racemase gene. The sequence of this gene is listed as nucleotides 98 to 1417 (including the TAA stopcodon) of SEQ ID NO:1 encoding the protein of SEQ ID: NO. 2 as presented infra.

Example 3A

Isolation of the α-H-α-amino Acid Amide Racemase Gene from *Arthrobacter nicotianae* NCIMB 41126

Expression Library Construction

A glycerol stock of *Arthrobacter nicotianae* NCIMB 41126 was plated onto a yeast carbon base plate containing 0.2% (w/v) D-α-amino-ε-caprolactam as sole N-source and cultivated for 3-4 days at 28° C. to get isolated colonies of the desired size. A single colony was transferred to 50 ml LB medium, and grown overnight at 28° C. under vigorous shaking. During the last half hour of this growth period, carbenicillin (final concentration 200 µg/ml) was added to weaken the cell wall. The cells were harvested by centrifugation, and the pellet obtained was re-suspended in 5 ml of 50 mM Tris-HCl, pH 8.0 containing 50 mM EDTA. After addition of 100 µl of lysozyme (100 mg/ml) and 25 µl of proteinase K (20 mg/ml) the suspension was incubated for 30 minutes at 37° C. Then 6 ml of Nuclei Lysis Solution (Promega Corporation, Madison, USA) was added followed by an incubation for 15 minutes at 80° C. Finally, the solution was incubated at 65° C. till complete lysis. After RNase treatment (final concentration 4 µg/ml) for 30 minutes at 37° C., 2 ml Protein Precipitation Solution (Promega Corporation, Madison, USA) was added, and the solution was vortexed for 20 seconds followed by incubation on ice. After centrifugation (10'; 4,500×g, 4° C.), the supernatant was transferred to a mixture of 0.1 volumes of NaAc (3M, pH 5) and 2 volumes of absolute ethanol. The precipitated genomic DNA was hooked to a sterile pipette and transferred to a tube with 2 ml of 10 mM Tris-HCl (pH 8). After the gDNA had dissolved, measurement of the $A_{260nm}$ and $A_{280nm}$ showed that about 2.3 mg of good quality gDNA had been isolated. Agarose gel electrophoresis proved that the gDNA isolated did not contain rRNA and that its size was larger than 15 kb.

50 µg of the gDNA was partially digested with Sau3A I at 1/24 U per µg of DNA at 37° C. for 30 minutes. Part of the digested DNA was run on a preparative 0.6% agarose gel and DNA fragments between 4 and 10 kb in size were isolated from the gel using the QIAquick extraction kit (Qiagen), concentrated by NaAc/ethanol precipitation and redissolved in 10 µl of 10 mM Tris-HCl, pH 8.0 buffer.

Vector DNA was prepared by digestion of 1 µg of pZErO-2 (Invitrogen, Breda, The Netherlands) with BamH I according to the protocol of the supplier.

Linearized vector DNA (10 ng) and *A. nicotianae* NCIMB 41126 gDNA fragments (2.5 µl) were ligated in a total volume of 10 µl with 2,5 U of T4 DNA ligase for 1 hour at 16° C. Subsequently, the ligation mixture was precipitated with NaAc/ethanol and resuspended in 5 µl of TE-buffer. 2.5 µl of this solution (about 5 ng of vector) was used for the electroporation of electrocompetent *E. coli* DH10B cells (Life Technologies) using a BioRad gene pulser (conditions: 2.5 kV, 25 µF, 100 Ω, 0.1 cm cuvette, 40 µl cell suspension) according to the protocol of the supplier. Transformants were plated onto LB medium with 50 mg/l kanamycin and incubated at 28° C. for 24 h. In total about 100,000 colonies were obtained which formed the primary gene library. All 100,000 colonies were pooled in LB medium supplemented with 50 mg/l kanamycin. Part of this cell suspension was used for a total plasmid isolation according to the QiaPrep procedure (Qiagen). This "library in plasmid form" was stored at −20° C. till further use. To the remaining part of the cell suspension, glycerol was added to a final concentration of 8% (v/v). The resulting suspension was stored in aliquots at −80° C. as primary gene library.

Screening

The *A. nicotianae* NCIMB 41126 library was screened for α-H-α-amino acid amide racemase containing clones using the protocol given in Example 3, however with a slightly modified substrate solution. Besides all components mentioned in Example 3, the substrate solution in this screening also contained 20 µM of pyridoxal-5-phosphate.

In total 10,691 clones of the *A. nicotianae* NCIMB 41126 library were screened. Two of these clones were identified as potential positive clones.

Confirmation of Potential Positive Clones

Confirmation of both potential positive clones was done according to the protocol given in Example 3, with the exception that all 3 substrate solutions used contained 10 µM of pyridoxal-5-phosphate.

This experiment demonstrated that both clones significantly converted D-leucine amide into L-leucine and D-valine amide into L-valine. As indicated in Example 1, these conversions proved the presence of α-H-α-amino acid amide racemase activity in these clones. Retransformation experiments in which the plasmids from both clones were introduced into *E. coli* TOP10 cells, showed that this α-H-α-amino acid amide racemase activity is plasmid encoded, because all recombinant cells tested converted D-leucine amide into L-leucine and D-valine amide into L-valine.

The plasmids from both positive clones were then subjected to restriction enzyme analysis. This analysis clearly showed that both recombinant plasmids contained an overlapping insert. Therefore, only one of these plasmids, i.e., pAn(1)PLV36D6, was sequenced. Analysis of the nucleotide sequence of this plasmid with a total size of 7.1 kb, revealed the complete nucleotide sequence of the α-H-α-amino acid amide racemase gene. The sequence of this gene is listed as nucleotides 80 to 1417 (including the TGA stop codon) of SEQ ID NO:8 encoding the protein of SEQ ID NO:9 as presented infra. As is shown below, it is also possible to express active α-H-α-amino acid amide racemase starting from nucleotide position 41 (GTG) from SEQ ID NO:8.

Example 4

Construction of Plasmid pKEC-AZAR

The *O. anthropi* IA α-H-α-amino acid amide racemase gene was subcloned into *E. coli* expression vector pKECaroP using PCR. Expression vector pKECaroP is similar to construct pKECtrp, whose construction has been described in WO 00/66751, except that pKECaroP contains the pSC101 derived par function and the *E. coli* aroH promoter instead of the trp promoter. The α-H-α-amino acid amino racemase open reading frame was amplified using 5'-GC-CTCA<u>CATATG</u>CAAACACCGCTTTCATTGCG-3' [SEQ ID NO:6] as forward primer (with Nde I cleavage site underlined), and 5'-GCCTCA<u>CCCGGG</u>TTACCACATCA TAAAATGGGCGACATC-3' [SEQ ID NO:7] as reverse primer (with Xma I cleavage site underlined), and plasmid pOa(1)PLV49B10 as template. This PCR, that was performed with PCR SuperMix High Fidelity (Life Technologies) according to the supplier's protocol, yielded a single fragment. Correct size (1,341 bp) of the amplified fragment was confirmed by agarose gel electrophoresis.

After purification of the amplified fragment with the QIAquick PCR Purification Kit (Qiagen), the fragment was cloned into vector pCR®4Blunt-TOPO (Invitrogen). The cloning mix was subsequently used to transform One Shot™ Chemically Competent *E. coli* TOP10 Cells (Invitrogen). Recombinant cells were selected by plating the whole transformation mixture on LB plates containing 100 µg/ml carbenicillin, followed by overnight incubation at 28° C.

After overnight cultivation of material from six colonies in 5 ml LB medium containing 100 µg/ml carbenicillin, plasmid DNA was isolated using the QIAprep Spin Miniprep Kit (Qiagen). Digestion with restriction enzymes Nde I and Xma I proved that five out of these six colonies contained the desired recombinant vector.

Plasmid DNA of the five correct clones was pooled and digested to completion with Nde I and Xma I. The total digestion mixture was applied to a preparative 1% agarose gel for separation of the different fragments. The correct fragment (1,322 bp) was subsequently isolated from the gel by the QIAquick Gel Extraction Kit (Qiagen) and stored at −20° C. till further use as insert fragment.

Plasmid pKECaroP was digested to completion with Nde I and Xma I, yielding two fragments of 2,850 and 3,036 bp as shown by analytical agarose gel electrophoresis. After heat inactivation of the Nde I and Xma I restriction enzymes (20 minutes, 65° C.), Bsa I was added to the mixture to cut the undesired 2,850 bp fragment into two smaller pieces. The complete digestion mixture was loaded on a 1% preparative agarose gel, followed by isolation of the desired 3,036 bp fragment using the QIAquick Gel Extraction Kit (Qiagen), that was stored at −20° C. till further use as vector fragment.

Vector and insert fragment were ligated using T4 DNA Ligase and the resulting ligation mixture was used for transformation of One Shot™ Chemically Competent E. coli TOP10 Cells. The transformation mix was plated on LB plates containing 50 µg/ml kanamycin, that were incubated at 28° C. till sufficiently large colonies appeared.

Colony-PCR using PCR SuperMix (Life Technologies) and the above given primers ([SEQ ID NO:6] and [SEQ ID NO:7]) was performed to screen for colonies containing the correct recombinant vector. Material from twelve PCR positives was used to inoculate 12 tubes with 5 ml LB medium containing 50 µg/ml kanamycin. Plasmid DNA was isolated using the QIAprep Spin Miniprep Kit. Digestion with restriction enzyme Hind III yielded two fragments of 1,731 and 2,627 bp with all twelve plasmids, proving that all twelve colonies contained the desired recombinant vector.

Five of these twelve positive clones were cultured in 25 ml LB medium supplemented with 50 µg/ml kanamycin. After overnight incubation at 28° C., cells were harvested via centrifugation and washed in the same sonification buffer as used in Example 2. After resuspending the cell pellets in sonification buffer (ratio wet weight cells to sonification buffer 1:10), the cells were disintegrated by sonification. Crude cell extracts were obtained by removal of the particulates via centrifugation.

The five obtained crude cell extracts were tested for α-H-α-amino acid amide racemase activity by mixing 0.5 ml thereof with 4.5 ml substrate solution consisting of a 22.2 mM HEPES-NaOH buffer pH 7.7 containing 0.01 mM of pyridoxal-5-phosphate and 66 mM D-leucine amide. Reactions were incubated at room temperature. Samples were taken after 0, 18 and 44 hours that were transferred to an equal volume of 1 M $H_3PO_4$ to stop the reaction. These samples were analyzed by HPLC according to the method given in Example 1.

With the crude extract of two of the five clones, called E. coli/pKEC_AZAR_3 and E. coli/pKEC_AZAR_11, significantly more L-leucine and L-leucine amide was detected in the 18 and 44 hour samples than in the 0 hour sample. Finally, nucleotide sequencing of pKEC_AZAR_3 and pKEC_AZAR_11 was revealed the correct nucleotide sequence of the α-H-α-amino acid amide racemase gene and flanking vector parts in these two recombinant plasmids.

Example 4A

Construction of Plasmid pBADAn36D6-DEST

The A. nicotianae NCIMB 41126 α-H-α-amino acid amide racemase gene was subcloned into E. coli expression vector pBAD/Myc-His-DEST using PCR and GATEWAY Cloning Technology (Invitrogen). The α-H-α-amino acid amide racemase open reading frame was first PCR amplified using 5'-GGGG<u>ACAAGTTTGTACAAAAAAGCAGGCT</u><u>AGGAGGA</u>ATTAACC*ATG*AGTACGCCGCGTTGCGGG GAG-3' [SEQ ID NO:10] as forward primer (with Shine-Delgarno site underlined, ATG startcodon in italic and attB1 site double underlined), and 5'-GGGG<u>ACCACTTTGTACAAGAAAGCTGGGT</u>*TCA*CCAACCA GCATAGGGAGCGATCTG-3' [SEQ ID NO:11] as reverse primer (with stop codon in italic and attB2 site double underlined), and plasmid pAn(1)PLV36D6 as template. The identification of plasmid pAn(1)PLV36D6 has been described in Example 3A. The PCR, which was performed with Expand High Fidelity polymerase (Roche Applied Science, Mannheim, Germany) according to the supplier's protocol, yielded a single fragment. Correct size (1,449 bp) of the amplified fragment was confirmed by agarose gel electrophoresis.

After purification of the amplified fragment from a preparative agarose gel with the QIAquick Gel Extraction Kit (Qiagen), the fragment was used as a substrate for the so-called BP in-vitro recombination reaction, which was performed according to the GATEWAY manual of the supplier (Invitrogen). Recombination between the attB-PCR fragment and the pDONR207 Donor Vector and subsequent transformation of the obtained mixture into E. coli DH5α competent cells (Invitrogen) resulted in the ENTRY clone pAN36D6-ENTRY. Recombinant cells were selected by plating the whole transformation mixture on 2*TY plates containing 7 µg/ml of gentamicin, followed by overnight incubation at 37° C. Plasmid DNA was isolated from a few single colonies using the QIAprep Spin Miniprep Kit (Qiagen), after having cultivated them in 2*TY medium containing 7 µg/ml of gentamicin for 16 hours. Digestion with restriction enzymes Pvu II, Nsp I (New England Biolabs, Frankfurt, Germany) and BssS I (New England Biolabs, Frankfurt, Germany), respectively, proved that all tested colonies contained the desired recombinant vector. Then, the attB-PCR inserts of four of these correct clones were sequenced. All four pAn36D6-ENTRY plasmids sequenced proved to contain the sequence as expected based on SEQ ID: No. 8 and the two PCR primers used.

Subsequently the α-H-α-amino acid amide racemase containing PCR fragment was introduced in Destination vector pBAD/Myc-His-DEST (vide infra) via the so-called LR in-vitro recombination reaction using one of the correct pAn36D6-ENTRY clones and pBAD/Myc-His-DEST. Also this reaction was performed according to the supplier's procedure. The recombination mix was used to transform One Shot™ Chemically Competent E. coli TOP10 Cells (Invitrogen). Recombinant cells were selected by plating the whole transformation mixture on 2*TY plates containing 100 µg/ml ampicillin followed by overnight incubation at 37° C. After overnight cultivation of a few colonies in 2*TY medium containing 100 µg/ml ampicillin, plasmid DNA was isolated using the QIAprep Spin Miniprep Kit (Qiagen). Digestion with restriction enzymes Acc I and Rsr II (New England Biolabs, Frankfurt, Germany), respectively, proved that all colonies contained the desired recombinant vector pBADAn36D6-DEST.

A single colony of strain E. coli TOP10/pBADAn36D6-DEST was used to inoculate 50 ml 2×TY medium supplemented with 100 µg/ml carbenicillin. After overnight incubation at 28° C., 500 µl of this culture was used to inoculate 500 ml 2*TY medium supplemented with 100 µg/ml carbenicillin and 0.005% arabinose. After overnight incubation at 28° C., cells were harvested via centrifugation (15 min. at 6,200×g, 4° C.) and washed in a solution containing 20 mM HEPES-NaOH, pH 7.5, 20 µM pyridoxal-5-phosphate, and 1.3 mM of dithiothreitol. After resuspending the cell pellets in the same buffer buffer solution (ratio wet weight cells to sonification buffer 1:3), the cells were disintegrated by 10 min. sonification with a Soniprep 150 of MSE operated at maximum amplitude using time intervals of 10 sec. (i.e., 10 sec. sonification, 10 sec. cooling) and cooling in ice/acetone. Crude cell extracts were obtained by removal of the particulates via centrifugation. Finally, sucrose was added to the cell free extract to a final concentration of 0.25 M.

The cell extract was tested for racemase activity by mixing 0.5 ml thereof with 9.5 ml substrate solution. Reactions were incubated at 37° C. Samples were taken at regular time intervals, that were transferred to an equal volume of 1 M $H_3PO_4$ to stop the reaction. These samples were analyzed by HPLC according to the method given in Example 1.

This experiment showed that the substrate was entirely racemized within 20 minutes. Therefore, it is concluded that the *A. nicotianae* NCIMB 41126 α-H-α-amino acid amide racemase is encoded by the open reading frame depicted in SEQ ID NO:8.

Example 4B

Construction of GATEWAY Destination Vector pBAD/Myc-His-DEST

Destination vector pBAD/Myc-His-DEST, that was used for the expression of the α-H-α-amino acid amide racemase gene from *A. nicotianae* NCIMB 41126 in *E. coli* was prepared by introducing a cat/ccdB cassette into the commercially available *E. coli* expression vector pBAD/Myc-HisC. The cat/ccdB cassette was amplified by PCR using 5'-AA<u>GAAGACCGGATC</u>CTAC<u>CTGACGCTTTTTATCGCAACTCTCTACTGTTTCTCC</u> ATACCCGTTTTTTGGGCTAAC*ACAAGTTTGTACAAAA AAGCTGAAC*-3' [SEQ ID NO:12] as forward primer (with promoter sequence double underlined, Bpi I recognition and cleavage site underlined and attR sequences in italic), and 5'-TTGTTC<u>TACGTA</u>*ACCACTTTGTACAAGAAAG*CTGAA C-3' [SEQ ID NO:13] as reverse primer (with SnaB I cleavage site underlined and attR sequences in italic), and vector pDEST15 (Invitrogen) as template. The PCR, which was performed with Expand High Fidelity polymerase (Roche Applied Science, Mannheim, Germany) according to the supplier's protocol, yielded a single fragment. Correct size (1792 bp) of the amplified fragment was confirmed by agarose gel electrophoresis. After purification of the amplified fragment from a preparative agarose gel with the QIAquick Gel Extraction Kit (Qiagen), the fragment was digested to completion with Bpi I (MBI Fermentas, St. Leon-Rot, Germany) (resulting in a overhang complementary to BamH I) and SnaB I (New England Biolabs, Frankfurt, Germany) and ligated with T4 DNA ligase into the *E. coli* expression vector pBAD/Myc-HisC (Invitrogen), which had been digested with BamH I and SnaB I. The ligation mix was subsequently used to transform Chemically Competent *E. coli* DB3.1 cells (Invitrogen). Recombinant cells were selected by plating the whole transformation mixture on 2*TY plates containing 35 μg/ml chloramphenicol followed by overnight incubation at 37° C. After isolation of the recombinant plasmid from three individual colonies, the inserts were sequenced. One of these clones proved to contain the desired insert, and was named pBAD/Myc-His-DEST. Although 7 abbreviations were observed between the nucleotide sequence of the sequenced part of plasmid pBAD/Myc-His-DEST and the reference sequence (Invitrogen—nucleotide sequence of pDEST15), all the essential features (chloramphenicol resistance, ccdB selection and attR recombination) of pBAD/Myc-His-DEST were fully functional.

Example 5

α-H-α-Amino Acid Amide Racemase Activity Test Using D-leucine Amide as Substrate and Whole *E. coli* Cells Containing the α-H-α-amino Acid Amide Racemase Gene from *Ochrobactrum anthropi* IA as Biocatalyst Preparation of the Cells A single colony of *E. coli* DH10B containing plasmid pOA(1)PLV49B10 was transferred to LB medium with kanamycin (50 mg/l) to prepare a pre-culture. After overnight incubation at 28° C. and 200 rpm, this pre-culture was used to inoculated a flask with 500 ml of 2*TY medium (10 g/l Yeast extract, 16 g/l Tryptone, 5 g/l NaCl) containing kanamycin (50 mg/l). After overnight growth at 28° C. ($OD_{620nm}$=4.4) and 200 rpm, cells were harvested by centrifugation (15 min. at 6,200×g, 4° C.), and washed with 50 mM HEPES-NaOH buffer of pH 7.7.

To be able to determine the background activity of the *E. coli* host-vector system in the activity tests, an *E. coli* DH10B strain containing a pZErO-2 based construct with a mutant Green Fluorescent Protein (GFPuv) encoding gene as insert in the opposite direction as the vector borne lac promoter, was cultivated via the same procedure (*E. coli* DH10B/pZErO-GFPuv-wrong-orientation). Growth of this recombinant *E. coli* strain resulted in an overnight culture with an $OD_{620nm}$ of 3.8.

The cell pellets from both cultures were subsequently washed and resuspended in 25 ml of 50 mM HEPES-NaOH buffer, pH 7.7. Aliquots of 2 ml of both cell suspensions were centrifuged once more and the pellets were stored at −20° C. until execution of the activity tests described below. The remaining part of these cell suspensions was stored at −20° C. for use in Example 6.

α-H-α-amino Acid Amide Racemase Activity Towards D-leucine Amide

To determine the activity of *E. coli*/pOA(1)PLV49B10 and the *E. coli* control, the above-mentioned cell pellets were thawed and resuspended to a total volume of 1 ml with 50 mM HEPES-NaOH buffer, pH 7.7. Then, reaction mixtures of 10 ml each were prepared containing 50 mM HEPES-NaOH buffer (pH 7.7), 10 μM pyridoxal-5-phosphate (PLP), 2.5 wt % of D-leucine amide, if applicable 20 mM of EDTA to suppress the *E. coli* amidase activity, and 0.5 ml of the *E. coli*/pOA(1)PLV49B10 and *E. coli* DH10B/pZErO-GFPuv-wrong-orientation cell suspensions or water (for chemical blanks). Reactions were started by the addition of the cells. Reaction mixtures were incubated at 30° C. and 175 rpm. Directly after addition of the cells (t=0 hours) and after 27 and 43 hours samples were taken in which the reaction was stopped by removal of the cells via centrifugation followed by 0.22 μM filtration. Finally, the filtered samples were stored at −20° C. until analysis by chiral HPLC as described below:

column: Sumichiral OA5000 from Sumika (150×4.6 mm I.D., 5μ)+guard column eluent: 85 v/v % 2 mM $CuSO_4$+15 v/v % methanol flow: 1.0 ml/min.

column temp.: 40° C.

inj. volume: 5 μl detection: fluorescence detection after post-column reaction with o-phthalaldehyde and 2-mercaptoethanol (wavelength ex=338 nm and em>420 nm)

The results of this experiment are presented in Table 4.

TABLE 4

α-H-α-amino acid amide racemase activity towards D-Leucine amide of *E. coli* DH10B/pOA(1)PLV49B10 and *E. coli* blank (*E. coli* DH10B/pZErO-GFPuv-wrong-orientation).

| Strain | 20 mM EDTA | Incuba-tion time (h) | D-leucine amide (wt %) | L-leucine amide (wt %) | D-leucine (wt %) | L-leucine (wt %) |
|---|---|---|---|---|---|---|
| B | − | 0 | 2.67 | n.d. | n.d. | n.d. |
| B | − | 27 | 2.51 | n.d. | 0.003 | 0.005 |
| B | − | 43 | 2.63 | 0.060 | 0.005 | 0.004 |
| A | − | 0 | 2.63 | n.d. | n.d. | n.d. |
| A | − | 27 | 1.03 | 0.170 | 0.009 | 1.71 |
| A | − | 43 | 0.512 | 0.063 | 0.017 | 2.12 |
| A | + | 0 | 2.61 | n.d. | n.d. | n.d. |
| A | + | 27 | 1.77 | 0.555 | 0.003 | 0.313 |
| A | + | 43 | 1.59 | 0.772 | 0.006 | 0.345 | n.d.: Not detectable
Strain A: *E. coli* DH10B/pOA(1)PLV49B10
Strain B: *E. coli* DH10B/pZErO-GFPuv-wrong-orientation The data in Table 4 clearly show that *E. coli* DH10B/pZErO-GFPuv-wrong-orientation could not convert D-leucine amide. Even after 43 hours of reaction, the reaction mixture contained the same amount of D-leucine amide as at the start of the reaction. This was also the case for all chemical blanks (data not shown).

With *E. coli* DH10B/pOA(1)PLV49B10 cells on the other hand, the amount of D-leucine amide clearly decreased in time. Without additional EDTA, this substrate was converted to a relatively low amount of L-leucine amide and a large amount of L-leucine. With additional EDTA, a much higher concentration of L-leucine amide was obtained, because EDTA, a chelating compound partially inhibits the amidase activity of *E. coli*, thereby reducing the conversion of L-leucine amide to L-leucine.

The results obtained in this experiment prove that *E. coli* DH10B/pOA(1)PLV49B10 cells contain α-H-α-amino acid amide racemase activity towards D-leucine amide. Furthermore, they show that by combining this α-H-α-amino acid amide racemase with an L-selective amidase/aminopeptidase (as present in, e.g., *E. coli* DH10B), D-α-H-α-amino acid amides can be converted to L-α-H-α-amino acids.

Example 6

α-H-α-Amino Acid Amide Racemase Activity Test using DL-leucine Amide as Substrate and Whole *E. coli* Cells Containing the α-H-α-amino Acid Amide Racemase Gene from *Ochrobactrum anthropi* IA as Biocatalyst The *E. coli* DH10B/pOA(1)PLV49B10 and *E. coli* DH10B/pZErO-GFPuv-wrong-orientation cell suspensions from Example 5 (Preparation of the cells) were used. To determine their activity towards racemic DL-leucine amide, identical reaction mixtures were prepared as in Example 5, except that 2.5 wt % of DL-leucine amide was used, EDTA was omitted in all reactions, and the reactions were started with 2 ml of the cell suspensions. Samples were taken directly after the start of the reactions (t=0 hours) and after 8 and 24 hours.

The results of this experiment are presented in Table 5.

TABLE 5

α-H-α-amimo acid amide racemase activity towards DL-leucine amide of *E. coli* DH10B/pOA(1)PLV49B10 and *E. coli* blank (*E. coli* DH10B/pZErO-GFPuv-wrong-orientation).

| Sample code | Incubation time (h) | D-leucine amide (wt %) | L-leucine amide (wt %) | D-leucine (wt %) | L-leucine (wt %) | e.e.[a]$_{\text{L-leucine}}$ (%) |
|---|---|---|---|---|---|---|
| B | 0 | 1.13 | 1.15 | 0.001 | 0.004 | — |
| B | 8 | 1.15 | 0.12 | 0.001 | 1.43 | 99.9 |
| B | 24 | 1.23 | n.d. | 0.002 | 1.48 | 99.7 |
| A | 0 | 1.19 | 1.25 | 0.001 | 0.003 | — |
| A | 8 | 1.24 | 0.33 | 0.004 | 1.45 | 99.4 |
| A | 24 | 0.43 | 0.14 | 0.028 | 2.25 | 97.5 | n.d.: Not detectable
[a]The e.e. (enantiomeric excess) of the L-acid was calculated using the formula: e.e.$_{\text{L-acid}}$ = [(L-acid − D-acid)/(L-acid + D-acid)] × 100%
Strain A: *E. coli* DH10B/pOA(1)PLV49B10
Strain B: *E. coli* DH10B/pZErO-GFPuv-wrong-orientation From the data in Table 5 it becomes clear that the *E. coli* blank cells (*E. coli* DH10B/pZErO-GFPuv-wrong-orientation) can only convert L-leucine amide to L-leucine with an enantiomeric excess of over 95%. The D-leucine amide is left untouched, thereby resulting in a maximum yield of 50% only.

With the *E. coli* DH10B/pOA(1)PLV49B10 cells containing the α-H-α-amino acid amide racemase encoding gene, clearly both L- and D-leucine amide are converted to L-leucine, leading to a yield of over 50% and maximum 100%. Again, the enantiomeric excess of the obtained L-leucine is well over 95%.

This experiment proves that by combining the α-H-α-amino acid amide racemase from *O. anthropi* IA with an L-selective amidase/aminopeptidase (as present in, e.g., *E. coli* DH10B), DL-α-H-α-amino acid amides can be converted into L-α-H-α-amino acids in a more than 50% yield.

Example 7

Determination of the Substrate Specificity of the α-H-α-amino Acid Amide Racemase from *Ochrobactrum anthropi* IA Using Cell Free Extract from *E. coli* TOP10/pKEC_AZAR_3

Preparation of the Cell Free Extract

Two pre-cultures of *E. coli* TOP10/pKEC_AZAR_3 (see Example 4) were prepared by inoculation of 2 erlenmeyer flasks with 100 ml of 2*TY medium (10 g/l Yeast extract, 16 g/l Tryptone, 5 g/l NaCl) containing 50 mg/l of kanamycin with 10 µl of a glycerol stock per flask. After overnight cultivation at 28° C. and 200 rpm, the pre-cultures were pooled, and subsequently used to inoculate 2 erlenmeyer flasks each containing 1 l of the same medium. Also these flasks were cultivated at 28° C. and 200 rpm for 16-18 h. Cells were harvested by centrifugation (15 min. at 6,200×g, 4° C.), washed with 20 mM HEPES-NaOH, pH 7.5, pooled, weighed, and resuspended in a solution containing 20 mM HEPES-NaOH, pH 7.5, 20 µM pyridoxal-5-phosphate, and 1.3 mM of dithiothreitol in a 1:3 ratio of wet weight cells to solution. Then, cells were disintegrated by 10 min. sonification with a Soniprep 150 of MSE operated at maximum amplitude using time intervals of 10 sec. (i.e., 10 sec. sonification, 10 sec. cooling) and cooling in ice/acetone.

Particles were removed by centrifugation, after which sucrose was added to the cell free extract to a final concentration of 0.25 M. The resulting cell free extract (CFE) was stored in aliquots at −20° C. E. coli TOP10/pBAD/Myc-HisC (Invitrogen) cells were treated in exactly the same way and served as negative control.

Determination of the Substrate Specificity

The substrate specificity of the α-H-α-amino acid racemase from O. anthropi IA was determined by measuring the racemase activity of the above-mentioned CFE towards a number of enantiomerically pure amino acid amides. Each reaction mixture of 10 ml (including the CFE) contained 50 mM HEPES-NaOH, pH 8.0, 20 μM pyridoxal-5-phosphate, 0.4 mg/ml BSA, 1 mM dithiothreitol, 20 mM EDTA and 75 mM of one of the amino acid amides tested. Reactions were started by the addition of 1 ml of the thawed CFE of E. coli TOP10/pKEC_AZAR_3 or E. coli TOP10/pBAD/Myc-HisC (blank) and were incubated at 37° C. At regular time intervals samples of 1 ml were taken and transferred to vials containing 1 ml of 1M $H_3PO_4$ to stop the reaction. After sufficient dilution of the samples in 0.4 M borate buffer pH 9.4, the mixtures obtained were analyzed using HPLC to determine the exact concentrations of the two amino acid and two amino acid amide enantiomers according to the following method.

| | |
|---|---|
| column: | Inertsil ODS-3 150 × 4.6 mm I.D. |
| eluent A: | 50 mM sodium acetate, pH 6.0 with acetic acid/acetonitrile 95/5 v/v % |
| eluent B: | 50 mM sodium acetate, pH 6.0 with acetic acid/acetonitrile 30/70 v/v % |
| gradient: | Time (min) / Eluent A (v/v %) / Eluent B (v/v %) |
| | 0 / 100 / 0 |
| | 28 / 0 / 100 |
| | 33 / 0 / 100 |
| | 33.1 / 100 / 0 |
| | 41 (stop-time) |
| flow: | 1.0 ml/min. |
| column temp.: | 40° C. |
| inj. volume: | 20 μl |
| detection: | fluorescence detection after pre-column reaction with o-phthaldehyde and D-3-mercapto-2-methylpropionic acid. (wavelength ex = 338 nm and em > 420 nm) |
| Pre-column reagents: | |
| Reagent A: | 50 mM Ortho Phtalic Anhydride (170 mg/25 ml MeOH/water 50/50 |
| Reagent B: | 113 mg D-S-benzoyl-3-mercapto-2-methylpropionic acid in 1 ml of 1M NaOH and dissolve. Add 9 ml of MeOH/water 50/50 and adjust to pH 7.0 with 1M H3PO4 |
| Reagent C: | 0.25M $H_3PO_4$ |
| Derivatization procedure: | 35 μl Reagent A |
| | 35 μl Reagent B |
| | 210 μl sample solution (sample in 0.4M borate buffer pH 9.4) |
| | 140 μl Reagent C |
| Reaction time: | 5 minutes |

The initial activity for the different substrates tested was calculated from the linear parts of the progress curves, in which the conversion was plotted against the reaction time. Use of the linear part of the progress curves secured that only samples taken at time points at which the substrate concentration was still sufficiently high, were used for the calculations. The conversion was calculated by dividing the amount of amino acid and amino acid amide formed via the racemase reaction (so with the opposite stereochemistry compared to the substrate molecule) by the total amount of two amino acid enantiomers and the two amino acid amide enantiomers. In this way, the calculated conversions were corrected for potential hydrolysis of the amide substrate and/or product by amidases/aminopeptidases that were not completely inhibited by the EDTA in the reaction mixture.

With the CFE of E. coli TOP10/pBAD/Myc-HisC none of the enantiopure α-H-α-amino acid amide substrates used was racemized. E. coli TOP10 clearly doesn't contain an α-H-α-amino acid amide racemase. The results of this experiment with the CFE from E. coli TOP10/pKEC_AZAR_3 are given in Table 6.

TABLE 6

Relative initial activity of CFE from E. coli TOP10/pKEC_AZAR_3 towards different enantiomerically pure α-H-α-amino acid amides

| Substrate | Structure | Rel. initial activity (%)[a] |
|---|---|---|
| D-leucine amide | 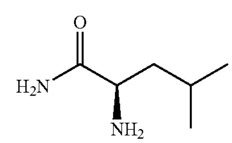 | 100 |
| D-alanine amide | 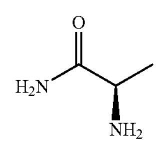 | 85 |
| L-2-aminobutyric acid amide | 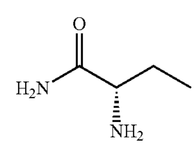 | 203 |
| D-norvaline amide | 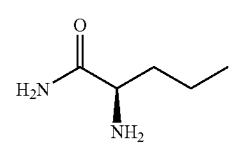 | 94 |
| L-serine amide | 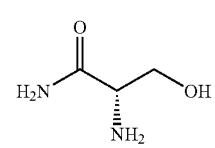 | 83 |

[a] All initial activities are given relative to the activity towards D-leucine amide The results presented in Table 6 clearly show that the CFE from E. coli TOP10/pKEC_AZAR_3 can not only racemize leucine amide, but also other α-H-α-amino acid amides. Because this recombinant strain contains the α-H-α-amino acid amide racemase gene from O. anthropi IA, this broad substrate specificity can only be attributed to the racemase encoded by this gene.

Example 8

Determination of the Substrate Specificity of the Partially Purified α-H-α-amino Acid Amide Racemase from *Ochrobactrum anthropi* IA Partial Purification The α-H-α-amino acid amide racemase from *O. anthropi* IA was partially purified from *E. coli* DH10B/pOa(1)PLV49B10. To obtain sufficient cell material for this purification, this recombinant strain was fermented at 10 liter scale. First, a seed culture was prepared by the inoculation of 500 ml of 2*TY medium containing 50 mg/l of kanamycin with 10 µl of a glycerol stock of this strain. After 22 hours of incubation at 28° C. and 170 rpm, an $OD_{620\,nm}$ of 2.2 was obtained. The complete seed medium was then transferred into a fermentor (Type ISF-200, Infors, Bottmingen, Switzerland) containing 9 liter of 2*TY medium containing 50 mg/l of kanamycin. pH was controlled at 7.0 by the addition of 5 N of $H_3PO_4$ and/or 5 N KOH, and the $pO_2$ was manually adjusted by changing both the aeration (1-2 liter of air per minute) and stirrer speed (250-750 rpm). The fermentor was operated at 28° C. for 19 hours, resulting in a cell suspension with an $OD_{620\,nm}$ of 5.7. The cells were harvested by centrifugation (15 min. at 12,000×g, 4° C.), washed once in 20 mM HEPES-NaOH, pH 7 and stored as wet cell pellet (about 125 g) at −20° C.

After thawing the cell pellet, cells were resuspended in buffer A (20 mM HEPES-NaOH, pH 7.5, 1.3 mM dithiothreitol, 20 µM pyridoxal-5-phosphate) containing 2.66 mM $MgCl_2$. Per gram of wet weight cells, 3 grams of buffer A were used. Just before disintegration, benzonase (30 U/gram of wet weight cells—Merck KGaA, Darmstadt, Germany) was added to the cell suspension. Cells were disintegrated by one passage through a homogenizer (Haskel, model NJ1600HD15, Wesel, Germany) at an operating pressure of 1,500 bar. Then particles were removed by centrifugation (30 min. at 34,000×g, 4° C.) and the resulting cell free extract (CFE) was stored in aliquots at −20° C.

All following purification steps were executed at 4° C. The first purification step was an ammonium sulphate precipitation at 40% saturation. This step was executed by adding an 80% saturated $(NH_4)_2SO_4$ solution drop by drop to an equal volume of CFE. The turbid solution was slowly shaken for 1.5 h, after which the precipitated protein was collected by centrifugation (30 min. at 15,000×g). The protein pellet was dissolved in buffer A, and used in the next purification step.

To enable anion exchange chromatography as second purification step, the protein solution after ammonium sulphate precipitation had to be desalted. Therefore, it was applied in 2.5 ml portions to PD-10 desalting columns (Amersham Biosciences, Roosendaal, The Netherlands), that had been equilibrated with 20 mM Tris-HCl, pH 8.0 (buffer B). Elution of the protein was effected with 3.5 ml of buffer B per PD-10 column. The desalted protein solution was applied to a Mono Q HR 10/10 column (Amersham Biosciences, Roosendaal, The Netherlands) that had been equilibrated with buffer B. This column was operated at a flow rate of 4 ml/min, and fractions of 4 ml were collected. The α-H-α-amino acid amide racemase was eluted from this column with buffer B containing 1 M NaCl applying a linear gradient of 0-100% NaCl in 100 ml. The α-H-α-amino acid amide racemase eluted at about 0.34 M NaCl and the active fractions were pooled.

The α-H-α-amino acid amide racemase containing protein solution was then applied to a HiLoad 26/60 Superdex 200 prep grade gel filtration column (Amersham Biosciences, Roosendaal, The Netherlands) that had been equilibrated with buffer B containing 1 M NaCl. The α-H-α-amino acid amide racemase was eluted with the equilibration buffer at a flow rate of 3 ml/min. Fractions of 3 ml were collected. The fractions containing the racemase activity were pooled and sucrose was added to a concentration of 0.25 M before storage in aliquots at −20° C.

Using this purification protocol, the *O. anthropi* IA α-H-α-amino acid amide racemase was partially purified from the *E. coli* DH10B/pOa(1)PLV49B10 CFE in an overall yield of 19%. SDS-PAGE using the NuPAGE system (Invitrogen) under reducing conditions with MES buffer showed that about 50% of the protein in the preparation after gel filtration consisted of the racemase.

Substrate Specificity Determination

The substrate specificity of the *O. anthropi* IA α-H-α-amino acid amide racemase was determined using the partially purified enzyme preparation obtained by the protocol described above. Reaction mixtures of 1 ml total volume were prepared by mixing 772 µl of 66.6 mM HEPES-NaOH, pH 8.0, 10 µl of 0.1 M dithiothreitol, 18 µl of a solution containing 20 mg/ml BSA and 1 mM pyridoxal-5-phosphate, and 100 µl of a 0.75 M substrate solution, pH 8.0. After equilibration for 5 minutes at 37° C., the reactions were started by the addition of 100 µl of the enzyme solution. Reaction mixtures were incubated at 37° C. without shaking. After regular time intervals, samples of 50 µl were taken and transferred into vials containing 950 µl of 1 M $H_3PO_4$ to stop the reaction. After sufficient dilution of the samples in 0.4 M borate buffer pH 9.4, the mixtures obtained were analyzed using HPLC to determine the exact concentrations of two amino acid amide enantiomers according to the method of Example 7.

Initial activity for the different substrates tested was calculated from the linear parts of the progress curves, in which the amount of the amino acid amide enantiomer formed (so with a stereochemistry opposite to the substrate molecule) was plotted against the reaction time. The results of this experiment are given in Table 7.

TABLE 7

Relative initial activity of the partially purified α-H-α-amino acid amide racemase from *O. anthropi* IA towards different enantiomerically pure α-H-α-amino acid amides.

| Substrate | Structure | Rel. initial activity (%)[a] |
|---|---|---|
| L-leucine amide | (structure shown) | 100 |
| L-alanine amide | (structure shown) | 350 |

TABLE 7-continued

Relative initial activity of the partially purified α-H-α-amino acid amide racemase from *O. anthropi* IA towards different enantiomerically pure α-H-α-amino acid amides.

| Substrate | Structure | Rel. initial activity (%)[a] |
|---|---|---|
| L-2-aminobutyric acid amide | 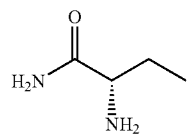 | 641 |
| D-norvaline amide | 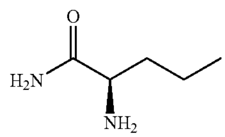 | 341 |
| L-valine amide | 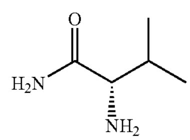 | 4.5 |
| LL-threonine amide | 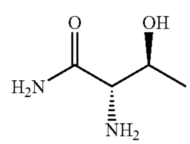 | 100 |
| LL-isoleucine amide | 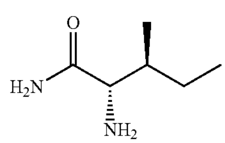 | 4.5 |
| D-2-amino-5-[1,3]dioxolan-2-yl-pentanoic acid amide | 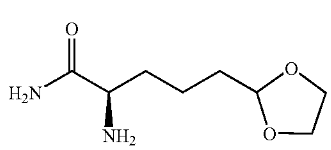 | 9.1 |
| L-phenylalanine amide | 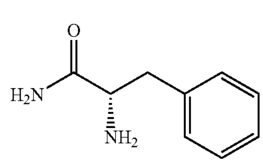 | 4.5 |
| D-phenylglycine amide | 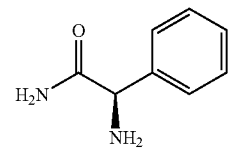 | 9.1 |

[a] All initial activities are given relative to the activity towards L-leucine amide The data in Table 7 clearly show that the α-H-α-amino acid amide racemase from *O. anthropi* IA has a relaxed substrate specificity, because activity was found towards amino acid amides with a short and long chain alkyl side chain, that can optionally be substituted at its $C_\beta$ atom, as well as towards amino acid amides with an aryl side chain.

Example 9

Determination of the Substrate Specificity of the α-H-α-amino Acid Amide Racemase from *Arthrobacter nicotianae* NCIMB 41126 Using Cell Free Extract from *E. coli* DH10B/pAn(1)PLV36D06

Preparation of Cell Free Extract

Preparation of the CFE of *E. coli* DH10B/pAn(1)PLV36D06 was performed as described in Example 7 for *E. coli* TOP10/pKEC_AZAR_3

Substrate Specificity Determination

Before applying the CFE from *E. coli* DH10B/pAn(1)PLV36D06 in the reactions with different enantiomerically pure α-H-α-amino acid amides to determine the substrate specificity of the *A. nicotianae* α-H-α-amino acid amide racemase, the *E. coli* amidases/aminopeptidases in this CFE were inhibited by a pre-treatment with an inhibitor cocktail. One tablet of Complete Mini Protease Inhibitor Cocktail (Roche Applied Science, Mannheim, Germany) was dissolved in 9 ml of the CFE followed by an incubation of 1 hour at room temperature. Next, reaction mixtures of 10 ml each (including the CFE) were prepared containing 50 mM HEPES-NaOH, pH 8.0, 20 μM pyridoxal-5-phosphate, 0.4 mg/ml BSA, 1 mM dithiothreitol and 75 mM of one of the amino acid amides tested. Reactions were started by the addition of 1 ml of the pre-treated CFE of *E. coli* DH10B/pAn(1)PLV36D06 or *E. coli* TOP10/pBAD/Myc-HisC (blank) and were incubated at 37° C. At regular time intervals samples of 1 ml were taken and transferred to vials containing 1 ml of 1M $H_3PO_4$ to stop the reaction. After sufficient dilution of the samples in 0.4 M borate buffer pH 9.4, the mixtures obtained were analyzed using HPLC to determine the exact concentrations of the two amino acid and two amino acid amide enantiomers according to the method of Example 7. Also the calculation of the initial activity of the CFE towards the different substrate α-H-α-amino acid amides was done as described in Example 7, including the correction for potential hydrolysis of the amide substrate and/or product by amidases/aminopeptidases that were not completely inhibited by the pre-incubation of the CFE with the inhibitor cocktail.

As already found in Example 7, also the pretreated CFE of *E. coli* TOP10/pBAD/Myc-HisC did not show any racemization of the enantiopure α-H-α-amino acid amide substrates used. The results of this experiment with the CFE from *E. coli* TOP10/pAn(1)PLV36D06 are given in Table 8.

TABLE 8

Relative initial activity of CFE from *E. coli* DH10B/pAn(1)PLV36D06 towards different enantiomerically pure α-H-α-amino acid amides

| Substrate | Structure | Rel. initial activity (%)[a] |
|---|---|---|
| D-leucine amide | 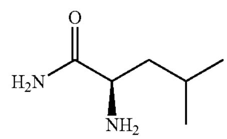 | 100 |
| L-2-aminobutyric acid amide | 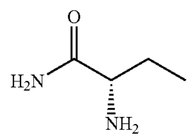 | 76 |
| D-norvaline amide | 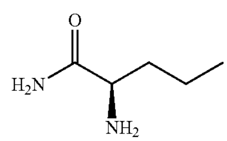 | 107 |
| D-valine amide | 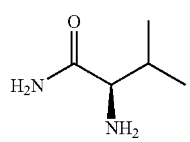 | 45 |

[a]All initial activities are given relative to the activity towards D-leucine amide The results presented in Table 8 clearly prove that the *A. nicotianae* NCIMB 41126 α-H-α-amino acid amide racemase has not only activity towards leucine amide, but also towards other α-H-α-amino acid amides.

Example 10

α-H-α-Amino Acid Amide Racemase Activity Test Using DL-2-aminobutyric Acid Amide as Substrate and CFE from *E. coli* DH10B/pOa(1)PLV49B10 Containing the α-H-α-amino Acid Amide Racemase from *O. anthropi* IA Preparation of the Cell Free Extract Cultivation of *E. coli* DH10B/pOa(1)PLV49B10 as well as the preparation of the cell free extract were performed in a manner comparable to Example 7. Also in this case, *E. coli* TOP10/pBAD/Myc-HisC was treated in exactly the same way to serve as negative control.

α-H-α-Amino Acid Amide Racemase Activity Towards DL-2-aminobutyric Acid Amide

To determine the activity of the CFE from *E. coli* DH10B/pOa(1)PLV49B10 and *E. coli* TOP10/pBAD/Myc-HisC, reaction mixtures of 10 ml each were prepared containing 50 mM HEPES-NaOH, pH 8.0, 20 μM pyridoxal-5-phosphate, 0.4 mg/ml BSA, 1 mM dithiothreitol, and 75 mM of DL-2-aminobutyric acid amide. Reactions were started by the addition of 1 ml of the thawed CFE of *E. coli* DH10B/pOa(1)PLV49B10 or *E. coli* TOP10/pBAD/Myc-HisC (blank) and were incubated at 37° C. for 21.5 h. At regular time intervals samples of 1 ml were taken and transferred to vials containing 1 ml of MeOH to stop the reaction. Analysis of these samples to determine the concentrations L- and D-2-aminobutyric acid and L- and D-2-aminobutyric acid amide was done by HPLC according to the following protocol.

column: Sumichiral OA5000 from Sumika (150×4.6 mm I.D., 5μ)+guard column eluent: 4 mM $CuSO_4$ in water flow: 1 ml/min.

column temp.: 10° C.

inj. volume: 6 μl detection: fluorescence detection after post-column reaction with o-phthalaldehyde and 2-mercaptoethanol in 0.4 M borate buffer with addition of EDTA (wavelength ex=338 nm and em>420 nm)

The results of this experiment are presented in Table 9.

TABLE 9

α-H-α-amino acid amide racemase activity towards DL-2-aminobutyric acid (Abu) amide of CFE from *E. coli* DH10B/pOA(1)PLV49B10 and *E. coli* blank (*E. coli* TOP10/pBAD/Myc-HisC).

| Sample code | Incubation time (h) | D-Abu amide (mM) | L-Abu amide (mM) | D-Abu (mM) | L-Abu (mM) | Conversion[a] (%) | e.e.$_{L-Abu}$ (%) |
|---|---|---|---|---|---|---|---|
| B | 0 | 41.1 | 37.5 | 0.0 | 2.1 | 2.6 | 100 |
| B | 0.75 | 43.2 | 26.1 | 0.0 | 14.4 | 17.2 | 100 |
| B | 2 | 42.2 | 7.2 | 0.0 | 30.5 | 38.2 | 100 |
| B | 4.65 | 38.9 | 0.1 | 0.3 | 39.4 | 50.1 | 98.5 |
| B | 8.25 | 42.4 | 0.1 | 0.7 | 40.9 | 48.7 | 96.7 |
| B | 21.5 | 40.9 | 0.1 | 1.7 | 38.3 | 47.4 | 91.7 |
| A | 0 | 42.3 | 40.5 | 0.0 | 1.4 | 1.6 | 100 |
| A | 0.75 | 39.6 | 29.3 | 0.0 | 12.3 | 15.2 | 100 |
| A | 2 | 34.7 | 17.8 | 0.0 | 29.1 | 35.7 | 100 |
| A | 4.65 | 20.8 | 11.5 | 0.1 | 52.3 | 61.8 | 99.6 |
| A | 8.25 | 12.4 | 8.6 | 0.5 | 64.9 | 75.1 | 98.5 |
| A | 21.5 | 6.7 | 5.8 | 1.4 | 71.7 | 83.9 | 96.3 |

[a]Conversion to the L-acid has been calculated using the formula: Conversion = [L-acid/(L-acid + D-acid + L-amide + D-amide)] × 100%
Strain A: *E. coli* DH10B/pOA(1)PLV49B10
Strain B: *E. coli* TOP10/pBAD/Myc-HisC From the data in Table 9 it becomes clear that the maximal conversion obtained with the CFE from the *E. coli* blank cells (*E. coli* TOP10/pBAD/Myc-HisC) doesn't exceed 50%. Because these cells do not contain an α-H-α-amino acid amide racemase activity, only the L-aminobutyric acid amide will be converted, leaving the other substrate enantiomer untouched. So the maximum theoretical yield in this case is 50% only, as is standard for (enzymatic) kinetic resolution reactions. The data from the last two time points of this series show that the L-amidase/aminopeptidase from *E. coli* TOP10 also slowly converts the D-aminobutyric acid amide when the concentration of the L-substrate approaches zero, resulting in L-aminobutyric acid with an enantiomeric excess of 91.7% after 21.5 hours of reaction.

With the CFE from *E. coli* DH10B/pOA(1)PLV49B10 containing the α-H-α-amino acid amide racemase from *O. anthropi* iA, clearly also the D-aminobutyric acid amide is converted, leading to an overall conversion to L-aminobutyric acid of 85.4% after 21.5 hours. The enantiomeric excess of the obtained L-aminobutyric acid in the reaction mixture is still well over 95% throughout the reaction. This is caused by the higher L-aminobutyric acid amide concentration at the end of the reaction through action of the α-H-α-amino acid amide racemase.

This experiment proves that by combining the α-H-α-amino acid amide racemase from *O. anthropi* IA with an L-selective amidase/aminopeptidase (as present in, e.g., the CFE from *E. coli* TOP10 cells) DL-α-H-α-amino acid amides can be converted into L-α-H-α-amino acids in more than 50% yield and excellent enantiomeric excess.

Example 11

α-H-α-Amino Acid Amide Racemase Activity Test Using DL-2-aminobutyric Acid Amide as Substrate and CFE from *E. coli* DH10B/pOa(1)PLV49B10 Combined with the L-aminopeptidase from *Pseudomonas putida* ATCC 12633

In this experiment, the *E. coli* DH10B/pOa(1)PLV49B10 CFE from Example 11 was used. It was combined with a preparation containing the L-aminopeptidase from *P. putida* ATCC 12633. This is the same L-enantioselective enzyme as was used as L-aminopeptidase help solution in the screening of the *O. anthropi* IA and *A. nicotianae* NCIMB 41126 gene libraries (Examples 3 and 3A).

A reaction mixture of 10 ml (total volume including enzyme preparations) was prepared containing 50 mM HEPES-NaOH, pH 8.0, 20 µM pyridoxal-5-phosphate, 0.4 mg/ml BSA, 1 mM dithiothreitol, and 75 mM of DL-2-aminobutyric acid amide. Reaction was started by the addition of 0.4 ml of the thawed CFE of *E. coli* DH10B/pOa(1) PLV49B10 and 0.17 ml of a solution containing L-aminopeptidase from *P. putida* ATCC 12633. The reaction mixture was incubated at 37° C. for 18 h. At certain time intervals samples of 1 ml were taken and transferred to vials containing 1 ml of MeOH to stop the reaction. Analysis of these samples to determine the concentrations L- and D-2-aminobutyric acid and L- and D-2-aminobutyric acid amide was done by HPLC according to the protocol of Example 11. The results of this experiment are presented in Table 10.

TABLE 10

α-H-α-amino acid amide racemase activity towards DL-2-aminobutyric acid (Abu) amide of CFE from *E. coli* DH10B/pOA(1)PLV49B10 combined with the L-aminopeptidase from *Pseudomonas putida* ATCC 12633.

| Incubation time (h) | D-Abu amide (mM) | L-Abu amide (mM) | D-Abu (mM) | L-Abu (mM) | Conversion (%) | e.e.$_{L\text{-}Abu}$ (%) |
|---|---|---|---|---|---|---|
| 0 | 36.2 | 34.1 | 0.0 | 0.5 | 0.7 | 100 |
| 0.5 | 34.6 | 22.2 | 0.0 | 11.7 | 17.1 | 100 |
| 1.0 | 36.4 | 7.3 | 0.1 | 32.2 | 42.4 | 99.4 |
| 1.5 | 33.0 | 2.7 | 0.0 | 38.5 | 51.9 | 100 |
| 2.0 | 30.4 | 1.7 | 0.0 | 41.9 | 56.7 | 100 |
| 18 | 0.4 | 0.0 | 1.6 | 70.8 | 97.3 | 95.7 |

The data in Table 10 show that by the combination of the α-H-α-amino acid amide racemase from *O. anthropi* IA and the L-aminopeptidase from *P. putida* ATCC 12633 an extremely high conversion to L-2-aminobutyric acid (97.3%) can be obtained. This conversion obtained is very close to the maximal theoretical value that can be obtained for a dynamic kinetic resolution (i.e., 100%). Furthermore, the enantiomeric excess of the L-2-aminobutyric acid is still above 95%.

Example 12

α-H-α-Amino Acid Amide Racemase Activity Test Using DL-2-amino-5-[1,3]dioxolan-2-yl-pentanoic Acid Amide as Substrate and CFE from *E. coli* DH10B/pOa(1)PLV49B10 Combined with the L-aminopeptidase from *Pseudomonas putida* ATCC 12633

In a very similar set-up, the combined activity of the α-H-α-amino acid amide racemase from *O. anthropi* IA and the L-aminopeptidase from *P. putida* ATCC 12633 was determined towards the more complex substrate DL-2-amino-5-[1,3]dioxolan-2-yl-pentanoic acid amide. The molecular structure of this amide can be found in the substrate table in Example 8. In this experiment 1 ml of the thawed CFE from *E. coli* DH10B/pOa(1)PLV49B10 was used together with 1 ml of a solution containing L-aminopeptidase from *P. putida* ATCC 12633. Reaction proceeded for 120 hours. Analysis of these samples to determine the concentrations L- and D-2-amino-5-[1,3]dioxolan-2-yl-pentanoic acid and L- and D-2-amino-5-[1,3]dioxolan-2-yl-pentanoic acid amide was done by HPLC according to the following protocol.

column: Crownether Cr(–) (150 mm×4.0 mm ID)
eluent: Perchloric acid in water, pH=1.0
flow: 1.2 ml/min.
column temp.: 18° C.
inj. volume: 20 µl
detection: fluorescence detection after post-column reaction with o-phthalaldehyde and 2-mercaptoethanol in 0.4 M borate buffer. (wavelength ex=338 nm and em>420 nm)

The results of this experiment are presented in Table 11.

TABLE 11

α-H-α-amino acid amide racemase activity towards DL-2-amino-5-[1,3]dioxolan-2-yl-pentanoic acid amide of CFE from *E. coli* DH10B/pOA(1)PLV49B10 combined with the L-aminopeptidase from *Pseudomonas putida* ATCC 12633.

| Incubation time (h) | D-Abu amide (mM) | L-Abu amide (mM) | D-Abu (mM) | L-Abu (mM) | Conversion (%) | e.e.$_{L\text{-}Abu}$ (%) |
|---|---|---|---|---|---|---|
| 0 | 36.6 | 36.5 | 0.0 | 4.3 | 5.6 | 100 |
| 3.6 | 35.7 | 2.7 | 0.0 | 37.6 | 49.5 | 100 |
| 22.1 | 29.9 | 1.0 | 0.1 | 40.3 | 56.6 | 99.5 |
| 53.2 | 27.4 | 0.1 | 0.1 | 43.5 | 61.1 | 99.5 |
| 120.2 | 23.7 | 0.1 | 0.4 | 46.0 | 65.5 | 98.2 |

The data in Table 11 show that by the combination of the α-H-α-amino acid amide racemase from *O. anthropi* IA and the L-aminopeptidase from *P. putida* ATCC 12633 over 65% conversion of the DL-2-amino-5-[1,3]dioxolan-2-yl-pentanoic acid amide to the L-acid is be obtained in 120 hours of reaction. The enantiomeric excess of the L-acid formed is higher than 98%.

The results obtained in this experiment prove that a dynamic kinetic resolution by combining the α-H-α-amino acid amide racemase from *O. anthropi* IA with an L-selective amidase/aminopeptidase (as, e.g., the L-aminopeptidase from *P. putida* ATCC 12633) is also possible for more complex α-H-α-amino acid amides containing functionilized side chains.

The invention claimed is:

1. An isolated polypeptide having α-H-α-amino acid amide racemase activity and having a degree of identity with the amino acid sequence comprising SEQ ID NO: 2 of at least 95%.

2. An isolated polypeptide having α-H-α-amino acid amide racemase activity, which is encoded by a nucleic acid which hybridizes under very high stringency conditions with SEQ ID NO:1 or the complementary strand thereof or the complementary strand thereof; wherein very high stringency conditions comprise hybridization in 6× sodium chloride/sodium citrate (SSC) at 45° C. for about 12 hours and two washes in 1× SSC and 0.1% SDS at 65° C. for 30 minutes.

3. An isolated polypeptide with α-H-α-amino acid amide racemase activity and having at least 95% identity with the amino acid sequence comprising in SEQ ID NO:2 obtainable by a method comprising:

a) culturing a microorganism-containing sample in or on growth medium comprising D-α-amino-ε-caprolactam,
b) testing one or more of the cultured microorganism(s) for α-H-α-amino acid amide racemase activity,
c) isolating at least one nucleic acid encoding the polypeptide from a microorganism tested for α-H-α-amino acid amide racemase activity wherein the polypeptide has at least 95% identity with the amino acid sequence comprising in SEQ ID NO:2,
d) expressing the nucleic acid in a host to produce the polypeptide, and
e) isolating the polypeptide from the host.

4. The polypeptide of claim 1 having a degree of identity with the amino acid sequence comprising in SEQ ID NO:2 of at least 97%.

5. The polypeptide of claim 2 encoded by a nucleic acid which hybridizes under high stringency conditions with SEQ ID NO:1 or the complementary strand thereof.

6. An isolated polypeptide having α-H-α-amino acid amide racemase activity and comprising an amino acid sequence presented in SEQ ID NO:2.

* * * * *